United States Patent
Fan et al.

(10) Patent No.: US 10,906,880 B2
(45) Date of Patent: Feb. 2, 2021

(54) KIND OF ISOTHIAZOLE OXIME ETHER-CONTAINING STROBILURIN DERIVATIVES AND ITS PREPARATION METHODS AND APPLICATION

(71) Applicant: Nankai University, Tianjin (CN)

(72) Inventors: Zhijin Fan, Tianjin (CN); Lai Chen, Tianjin (CN); Xiaofeng Guo, Tianjin (CN); Yujie Zhu, Tianjin (CN); Xiaolin Qian, Tianjin (CN); Liuyong Ma, Tianjin (CN); Nailou Zhang, Tianjin (CN); Haixia Wang, Tianjin (CN); Zhiming Zhang, Tianjin (CN); Jinghua Xu, Tianjin (CN); Yinqi Song, Tianjin (CN)

(73) Assignee: Nankai University, Tianjin (CN)

( * ) Notice: Subject to any disclaimer, the term of this patent is extended or adjusted under 35 U.S.C. 154(b) by 0 days.

(21) Appl. No.: 16/073,089

(22) PCT Filed: Jan. 25, 2017

(86) PCT No.: PCT/CN2017/072557
§ 371 (c)(1),
(2) Date: Jul. 26, 2018

(87) PCT Pub. No.: WO2017/129122
PCT Pub. Date: Aug. 3, 2017

(65) Prior Publication Data
US 2019/0031627 A1    Jan. 31, 2019

(30) Foreign Application Priority Data

Jan. 26, 2016 (CN) .......................... 2016 1 0058411
Mar. 25, 2016 (CN) .......................... 2016 1 0185795

(51) Int. Cl.
C07D 275/03 (2006.01)
A01N 43/80 (2006.01)

(52) U.S. Cl.
CPC .......... C07D 275/03 (2013.01); A01N 43/80 (2013.01)

(58) Field of Classification Search
CPC ............................. C07D 275/03; A01N 43/80
See application file for complete search history.

(56) References Cited

U.S. PATENT DOCUMENTS 5,723,473 A    3/1998 Pilkington

FOREIGN PATENT DOCUMENTS

| CA | 2005345 A1 | 6/1990 |
| CN | 1042900 A | 6/1990 |
| CN | 1065658 A | 10/1992 |
| CN | 1191670 A | 9/1998 |
| CN | 1306506 A | 8/2001 |
| CN | 104649996 A | 5/2015 |
| CN | 104650061 A | 5/2015 |
| WO | 9218487 A1 | 10/1992 |
| WO | 2008104101 A1 | 9/2008 |

OTHER PUBLICATIONS

Chen et al., RSC Adv., 2017, 7, pp. 3145-3151.*
International Search Report for PCT Applicaiton No. PCT/CN2017/072557 dated May 8, 2017, 10 pages with English Translation.
Written Opinion of International Searching Authority for PCT Applicaiton No. PCT/CN2017/072557 dated May 8, 2017, 3 pages.
Chen D. P., "Research progress on five-membered heterocyclic bactericidal active compounds," Modern Agrochemicals, Apr. 2014, 2(13):5-10.
Chinese First Office Action for Chinese Application No. 201610185795.7, dated Nov. 23, 2018, 14 pages with English Translation.
Chinese Search Report for Chinese Application No. 201610185795.7, dated Nov. 7, 2018, 1 page.
Fisher et al., "Re-examination of Inhibitor Resistance Conferred by Qo-site Mutations in Cytochrome b using Yeast as a Model System," Pest. Manage. Sci. 2005, 61(10) 973-978.
Hong Song et al., "Synthesis and Fungicidal Activity of Strobilurin Analogues Containing 1,2,4-Triazole Oxime Ether Moiety", Journal of Heterocyclic Chemistry, 51, Nov. 2014, 1603-1606.
Kuan A. Y., "Development of Methoxy Acrylate Fungicides and the Synthesis of Several major Varieties," Fine and Specialty Chemicals, Apr. 2012, 20(4): 24-28.

(Continued)

Primary Examiner — Alicia L Otton
(74) Attorney, Agent, or Firm — TraskBritt

(57) ABSTRACT

The present invention is that provided a synthesis method of a series of isothiazole oxime ether containing strobilurin derivatives IV. The present invention relates to 3,4-dichloroisothiazolyl oxime ether strobilurin derivatives, and their chemical structural formula is as shown by IV.

IV

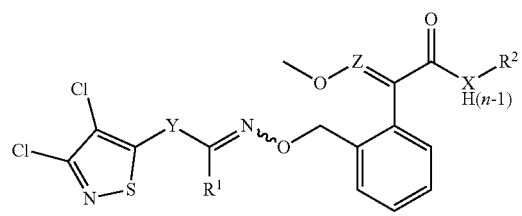

The invention discloses the structural formula of the above compound, the synthesis method and the use as an insecticide, a fungicide, an anti-plant virus agent, and an agriculturally acceptable auxiliary or synergist and a commercial insecticide. The use of a fungicide, an anti-plant virus agent and an acaricide in combination for controlling agricultural, forestry, horticultural plant pests, diseases, virus diseases and preparation methods.

14 Claims, No Drawings

(56) References Cited

OTHER PUBLICATIONS

Mel'nikov N. N., Journal of the All-Union Chemist of the Nesky Society, D. I. Mendeleeva, 1988, 33(6), 602-609.
Yuan X. Y., "Synthesis and Fungicidal Activity of the Strobilurins Containing 1,3,4-Thiodiazole Ring," Chinese Journal of Organic Chemistry, 2014, 34: 170-177.

* cited by examiner

KIND OF ISOTHIAZOLE OXIME ETHER-CONTAINING STROBILURIN DERIVATIVES AND ITS PREPARATION METHODS AND APPLICATION

CROSS-REFERENCE TO RELATED APPLICATIONS

This application is a national phase entry under 35 U.S.C. § 371 of International Patent Application PCT/CN2017/072557, filed Jan. 25, 2017, designating the United States of America and published as International Patent Publication WO 2017/129122 A1 on Aug. 3, 2017, which claims the benefit under Article 8 of the Patent Cooperation Treaty to Chinese Patent Application Serial No. 201610185795.7, filed Mar. 25, 2016, and to Chinese Patent Application Serial No. 201610058411.5 filed Jan. 26, 2016.

TECHNICAL FIELD

The present invention relates to N and S containing isothiazolyl oxime ether strobilurin compounds, especially involving 3,4-dichloroisothiazolium oxime ether compounds, that is 3,4-dichloroisothiazolyl oxime ether-containing strobilurin derivatives.

BACKGROUND OF THE INVENTION

Heterocycles have been widely used as biological activity in the lead optimization in agrochemical studies. Five-membered heterocyclic compounds have potency to induce plant defense responses, antifungal, plant growth regulating and insecticidal activities (D. P. Chen, *Mod. Agrochem.* 2014, 2(13):5-10). Among them, N and S atom-containing isothiazole founded by Mel'nikov displayed plant growth regulatory activity (N. N. Mel'nikov, *Zhurnal Vseoyuznogo Khimic Heskogo Obshchestva im. D. I. Mendeleeva*, 1988, 33(6), 602-609).

Strobilurin fungicides have a broad-spectrum of fungicidal activities and can control diseases caused by almost all kinds of fungal species (ascomycetes, basidiomycetes, oomycetes and deuteromycetes), such as wheat powdery mildew, leaf blight, red leaf spot, net blotch, black shank, rice blast, sheath blight, downy mildew, and blight disease (A. Y. Kuan, *Fine and Specialty Chemicals*, 2012, 20(4): 24-28). Strobilurin fungicides have many advantages such as high efficiency, broad spectrum, low toxicity, systemic activity and easy for degradation, this is one of the most important classes of agricultural fungicide (X. Y. Yuan, *Chin. J. Org. Chem*, 2014, 34:170-177). The main commercial strobilurins fungicides are listed as bellow: azoxystrobin, kresoxim-methyl, pyraclostrobin, trifloxystrobin, fluoxastrobin, picoxystrobin, metaminostrobin, dimoxystrobin, orysastrobin, enestrobin, pyraoxystrobin, SYP-1620 and so on. However, resistance risk increased due to the single mode of action of strobilurin fungicides and its abused application. Plant elicitors can stimulate the plant immunity-system to produce long-lasting systemic acquired resistance (SAR) and they did not show any direct effect against plant pathogen in vitro, they have no resistance risk, therefor, novel plant elicitor development is urgent task for plant protection as a green measure.

SUMMARY OF THE INVENTION

The technical problem need to be solved by the present invention is to provide a series of novel isothiazole oxime ether-containing strobilurin derivatives, synthetic methods, the compounds themselves and their regulation and control of biological activity and determination methods for plant pests and pathogens control in the areas of agriculture, horticulture, health and forestry. At the same time, these compounds are applied in the fields of agriculture, horticulture, forestry, and health.

The technical scheme adopted by the present invention to solve this technical problem is isothiazolyl methyl ether with the insecticidal, acaricidal, fungicidal, anti-plant virus, and inducing plant defense responses activity in the fields of agriculture, horticulture, and forestry. The invention, accordingly, provides novel compounds with the general formula shown as IV:

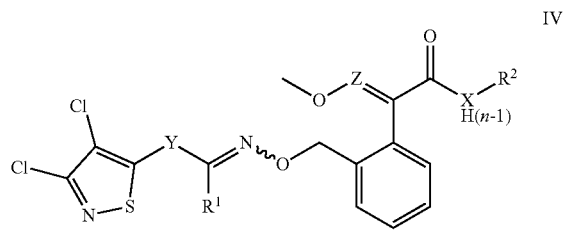

wherein $R^1$ is selected from the group consisting of $CH_3$, H, and $NH_2$;

$R^2$ is selected from the group consisting of

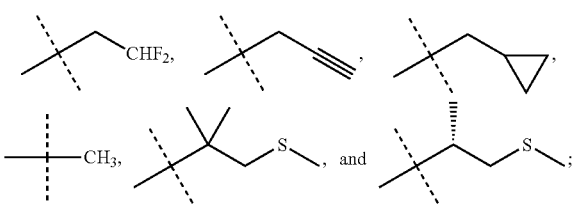

X is O or N, and n is 1 or 2;

Y is selected from the group consisting of: CHOH—$CH_2$, CHO—$CH_2$, and (CH=CH)$_m$, and m is 0 or 1; and Z is C or N.

Synthesis of 3,4-dichloroisothiazole oxime ether-containing strobilurin derivatives IV of the invention is shown as below:

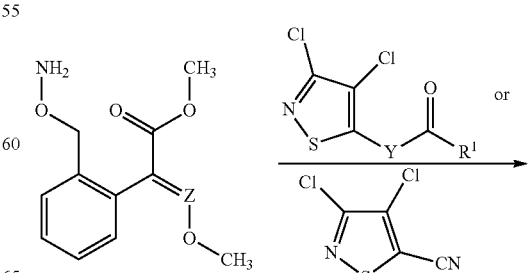

-continued

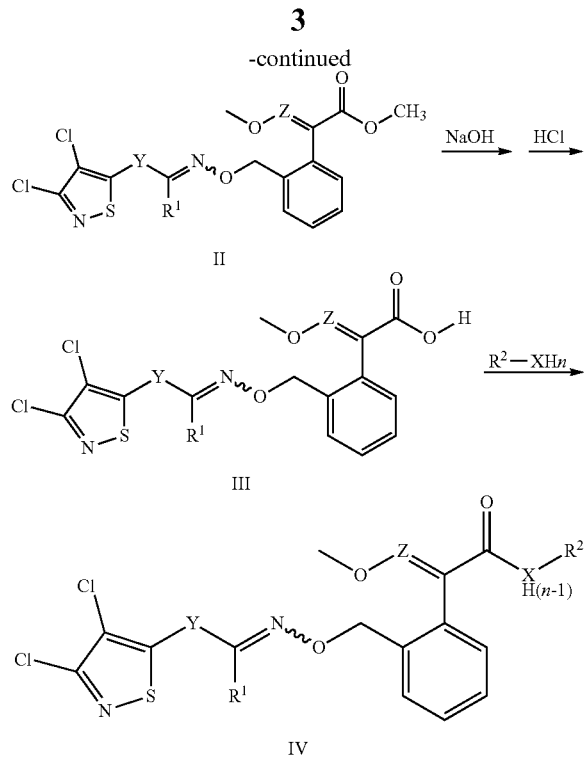

Wherein
R¹ is selected from the group consisting of CH₃, H, and NH₂;
R² is selected from the group consisting of

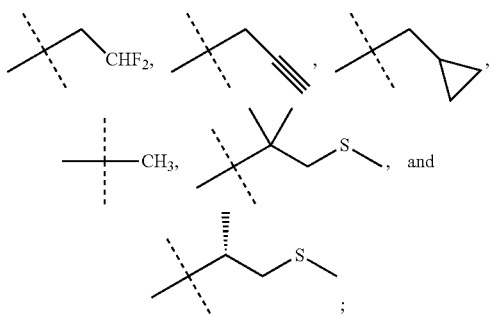

X is O or N, and n is 1 or 2;
Y is selected from the group consisting of CHOH—CH₂, CHO—CH₂, and (CH=CH)$_m$, and
m is 0 or 1; and
Z is C or N.

Preferably, 3,4-dichloroisothiazole oxime ether-containing strobilurin derivatives were synthesized by the following steps.

A. General Procedure for the Synthesis of Compounds II:

A solution of compound I (1.12 mmol) in 15 ml ethanol was added to the solution of intermediates 3,4-dichloroisothiazole-5-substituted carbonyl compounds (1.02 mmol) in ethanol (15 ml), and to the reaction mixture was added the catalytic amount of hydrochloric acid (2 mol/L) and stirred at room temperature for overnight. The solvent was evaporated under reduced pressure and the residue was then purified by recrystallization in ethanol or column chromatography on silica gel using ethyl acetate and petroleum ether (b.p. 60-90° C.) with 1:9 to 1:4 of v/v as an eluent to obtain compounds II.

B. General Procedure for the Synthesis of the Other Compounds II:

A solution of compounds I (1.22 mmol) in 15 ml ethanol was added to the solution of commercially available 3,4-dichloroisothiazole-5-carbonitrile (0.20 g, 1.11 mmol) in ethanol (15 ml), 2-mercaptoacetic acid (0.10 g, 1.09 mmol) was added to the reaction mixture for stirring at room temperature for overnight. The solvent was evaporated under reduced pressure and the residue was then purified by recrystallization in ethyl acetate or column chromatography on silica gel using ethyl acetate and petroleum ether (b.p. 60-90° C.) with 1:4 to 1:9 of v/v as an eluent to give compounds II.

C. General Procedure for the Synthesis of the Other Compounds III:

One of intermediates II (2.49 mmol) was dissolved in 15 ml methanol, the solution of sodium hydroxide (0.30 g, 7.47 mmol) in 15 ml methanol was added to the reaction mixture for 30 minutes of refluxing. After stopping of the reaction, the solvent was evaporated under reduced pressure and the residue was added 15 ml water. The aqueous phase was adjusted to pH 2-3 with dilute hydrochloric acid (3 mol/L). The aqueous layer was extracted with ethyl acetate (2×15 ml). The organic layers were combined and washed with saturated brine (50 ml), dried over sodium sulfate. After filtration, the solvent was evaporated to obtain the compounds III as a white solid.

D. General Procedure for the Synthesis of the Other Compounds IV:

The reaction mixture of the compound III (0.75 mmol), EDCI (0.17 g, 0.90 mmol), HOBT (0.11 g, 0.77 mmol) in dichloromethane (25 ml) was stirred for 15 minutes in ice bath. A solution of amine in dichloromethane (25 ml) was added and followed by Et₃N (0.09 g, 0.90 mmol), the reaction mixture was stirred for further 16 hours. After completion of the reaction, the organic layer was successively washed with water (2×30 ml) and saturated brine (40 ml), dried over MgSO₄ and concentrated under vacuum. After filtration, the solvent was evaporated. The residue was then purified by column chromatography on silica gel using ethyl acetate and petroleum ether (60-90° C.) with 1:2 to 1:5 of v/v as an eluent to give compounds IV.

The invention also provides the use of the isothiazole oxime ether-containing strobilurin derivatives IV in the preparation of a fungicide, a tobacco mosaic virus control agent or a plant elicitor.

The invention also provides the use of the isothiazole oxime ether-containing strobilurin derivatives IV and an agriculturally acceptable adjuvant in the preparation of a fungicide, a tobacco mosaic virus control agent or a plant elicitor.

The invention also provides the use of the isothiazole oxime ether-containing strobilurin derivatives IV for agricultural and forestry and horticultural plant pests controlling.

Preferably, the isothiazole oxime ether-containing strobilurin derivatives IV are co-administered with agricultural chemicals.

Preferably, the above-described agricultural chemicals are chosen from one or several insecticide, fungicide, anti-plant virus agent, and acaricide.

Preferably, the isothiazole oxime ether-containing strobilurin derivatives IV can be used alone or can be mixed with one, two or more insecticides to form an insecticidal mixture for agricultural and forestry and horticultural plant pests controlling.

Preferably, the above-described insecticides are chosen from Chlorpyrifos, Diazinon, Acetamiprid, Emamectin, Milbemectin, Abamectin, Spinosad, Fenvalerate, Esfenvalerate, Theta-Cypermethrin, Beta-Cypermethrin, Cyhalothrin, Deltamethrin, Beta-Cyfluthrin, Lambda-Cyhalothrin, Permethrin, S-Bioallethrin, Bifenthrin, Ethofenprox, Tau-fluvalinate, Imidacloprid, Nitenpyram, Imidaclothiz, Thiacloprid, Thiamethoxam, Clothianidin, Dinotefuran, Diflubenzuron, Chlorbenzuron, Teflubenzuron, Hexaflumuron, Flufenoxuron, Chlorfluazuron, Lufenuron, PENFLUORON, Noviflumuron (CAS: 121451-02-3), Flucycloxuron, Novaluron, Bay sir 6874, Bay SIR-8514, N-[[5-(4-bromophenyl)-6-methylpyrazin-2-yl]carbamoyl]-2-chlorobenzamide, Bistrifluron, (CAS: 467427-81-1), Tebufenozide, Halofenozide, Methoxyfenozide, Chromafenozide, Dimethoate, O,O-Dimethyl-S-methylcarbamoylmethyl phosphorothioate, Dichlorvos, Orthene, Triazophos, Quinalphos, Pyridaphenthion, Isazophos, Isoprocarb, Carbaryl, Pirimicarb, Metolcarb, Cartap, Fenobucarb, N-methyl 2,3-dimethylphenyl carbamate, Benfuracarb, Carbosulfan, Bromopropylate, Hexythiazox, Fenpyroximate, Pyridaben, Clofentezine, Propargite, Diafenthiuron, Pymetrozine, Spirodiclofen, Spirotetramatr, Flufiprole, Azocyclotin, Buprofezin, Mocap, Fipronil, Molosultap, Chloantraniliprole, Flubendiamide, Cyhalodiamide, Cyantraniliprole, Tolfenpyrad, Chlorfenapyr, Etoxazole, 4-Chloro-N-(4-tert-butyl benzyl)-3-ethyl-1-methyl-1H-pyrazole-5-carboxamide (CAS: 119168-77-3), Tebufenpyrad, 4-chloro-5-[(6-chloropyridin-3-yl)methoxy]-2-(3,4-dichlorophenyl)pyridazin-3-one (CAS: 107360-34-9), or Pyriproxyfen.

Preferably, the isothiazole oxime ether-containing strobilurin derivatives IV are presented in the insecticidal composition in an amount between 1%-90% by mass percentage.

Preferably, the mass ratio of the isothiazole oxime ether-containing strobilurin derivatives IV to the above-described insecticide is from 1%:99% to 99%:1% by mass percentage.

Preferably, the formulation processed by the insecticidal composition is chosen from suspension concentrates for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent.

Preferably, the plant pests controlled by the insecticidal composition are chosen from *Tetranychus cinnbarinus, Locusta migratoria manilensis*, cypress locust, rice blast, Japanese yellow ridge, single locust, oriental carp, rice locust, scorpion horse, greenhouse hummer, rice tube hummer, wheat tube hummer, greenhouse whitefly, whitefly, black-tailed leafhopper, big green leafhopper, cotton leafhopper, spotted wax hopper, brown plant hopper, whitebacked plant hopper, gray plant hopper, sugarcane, squared cornucopia, cotton aphid, wheat fork, wheat long tube, peach aphid, sorghum, radish, blown sorghum, mulberry scorpion, scorpion shield, pear round scorpion, white wax worm, red wax scorpion, Korean ball scorpion, *stephanitis nashi esaki et takeya*, banana nets, fine-horned flower buds, tiny flower buds, needle-edge mites, rice spider mites, rice brown mites, rice black mites, rice green mites, green blind mites, ticks, black scorpions, large grass mites, licao, chinese grasshopper, moth, yellow moth, brown moth, flat moth, wheat moth, cotton bollworm, sweet potato moth, diamondback moth, peach small heartworm, soybean heartworm, peach small carnivorous worm, apple leaf roller moth, brown leaf moth, yellow leaf moth, sorghum, pea pod, corn borer, stem borer, rapeseed meal, rice leaf roller, stripe, roller leafhopper, armyworm, *Spodoptera litura*, rice blast, cotton small bridge worm, beet armyworm, giant salamander, dingdian diamond, small tiger, earth tiger, yellow tiger, toxic moth, gypsy moth, sweet potato hawk moth, bean hawk moth, straight grain rice butterfly, cryptic valley butterfly, citrus phoenix butterfly, jade belt phoenix butterfly, cabbage butterfly, ramie red butterfly, ramie butterfly, bean phthalocyanine, venus carapace, wrinkle-skinned armor, wheat-spotted armor, ditch-gold needle, fine-necked Golden Needle, *G. striata*, Black-skinned scorpion, citrus small jiding, lampra limbata gebler, *Tenebrio molitor*, Black mealworm, *tribolium castaneum* herbst, *Tribolium confusum* jac. du val., patina, golden tortoise, dark golden tortoise, north China black scorpion golden tortoise, mulberry ox, star celestial, orange brown hornbill, peach red neck horn, big worm leaf worm, small cockroach Leaf worm, yellow squash, yellow scalloped beetle, mung bean elephant, pea elephant, broad bean elephant, corn elephant, rice elephant, Dolerus Chu, pear fruit sawfly, yellow belt wasp, armyworm white star wasp, Chrysalis suspense, *Campoletis chlorideae* Uchida, *Verruca verruca*, mosquito, fly, horsefly, wheat blossom midge, wheat midge, rice gall midge, Tetradacus *citri*, Melon fruit fly, wheat fly ash, Leafminer, soybean stem borer, wheat straw flies, seed fly, onion fly, carrot fly, *Exorista civilis* Rondani, or Mailing flies of corn borer.

Preferably, the plants controlled by the insecticidal composition are chosen from rice, wheat, barley, oats, corn, sorghum, sweet potato, potato, tapioca, soybean, pea, broad bean, mung bean, adzuki bean, cotton, sericulture, peanut, rapeseed, sesame, sunflower, beet, sugar cane, coffee, cocoa, ginseng, fritillary, rubber, coconut, oil palm, sisal, tobacco, tomato, radish, cucumber, cabbage, celery, mustard, beet, rape, onions, garlic, watermelon, melon, cantaloupe, papaya, apple, citrus and peach, tea, wild vegetables, bamboo shoots, hops, pepper, banana, orchid, or bonsai.

Preferably, the isothiazole oxime ether-containing strobilurin derivatives IV can be used alone or can be mixed with one, two or more fungicides to form a fungicidal mixture for controlling agricultural and forestry and horticultural plant diseases.

Preferably, the above-described fungicides are chosen from Benzothiadiazole, Tiadinil, abbreviated as TDL, thiazamide, SZG-7, 4-methyl-1,2,3-thiadiazole-5-carboxylic acid, 4-methyl-1,2,3-thiadiazol-5-formate, 4-methyl-1,2,3-thiadiazole-5-carboxylic acid ethyl ester, DL-β-aminobutyric acid, isotianil, 3,4-dichloroisothiazol-5-carboxylic acid, 3,4-dichloroisothiazol-5-formate, 3,4-dichloroisothiazol-5-carboxylic acid ethyl ester, ribavirin, Antofine, Ningnanmycin or salicylic acid, cymoxanil, thiram, Zinc bis dimethyldithiocarbamate, mancozeb, ethylphosphorus, Thiophanate-methyl, chlorothalonil, Fenaminosulf, procymidone, fenpropidin, Thiophanate-methyl, thiophanate, Metalaxyl-M, flumorph, Dimethomorph, benalaxyl M, diclocymet, flusulfamide, TF-991, thifluzamide, flutolanil, tecloftalam, carpropamid, cyflufenamid, fenhexamide, fenoxanil, silthiopham, furametpyr, penthiopyrad, mandipropamid, zoxamide, fenfuram, carboxin, chlozolinate, iprodione, procymidone, azoxystrobin, dimoxystrobin, fluoxastrobin, kresoxim-methyl, metominostrobin, orysastrobin, picoxystrobin, pyraclostrobin, trifloxystrobin, enestroburin, SYP-1620, Azaconazole, bromuconazole, cyproconazole, difenoconazole, diniconazole, diniconazole M, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, bitertanol, thiabendazole, fuberidazole, imazalil, S-imazalil, prochloraz, triflumizole, cyazofamid, fenamidone, oxpoconazole, pefurazoate, famoxadone, SYPZ048, hymexazol, oxadixyl, ethaboxam, etridiazole, octhilinone, benthiazole, dodemorph, fenpropimorph, tridemorph, fenpiclonil, fludioxonil, fluazinam, pyrifenox, ICIA0858, boscalid, fluopicolide, PEIP, cyprodinil, diflumetorim, ferimzone, mepanipyrim, pyrimethanil, fenarimol, nuarimol, chinomethionat, dithianon, ethoxyquin, 8 hydroxyquinoline, Sulfate, proquinazid, quinoxyfen, diethofencarb, iprovalicarb, benthiavalicarb, Isopropyl, propamocarb, methasulfocarb, edifenphos, iprobenfos, pyrazophos, tolclofosmethyl, S-blasticidin, Kasugamycin, myxothiazol, polyoxins, olyoxorim, pseudomycin, PSFD271, validamycin, jinggangmycin, streptomycin, metalaxyl, furalaxyl, benalaxyl, ofurace, mepronil, carbendazim, benomyl, thiophanate-methyl, triadimefon, bupirimate, dimethirimol, ethirimol, captafol, captan, folpet, vinclozolin, fluoroimide, dimethachlon, isoprothiolane, EBP, bismerthiazol, quintozene, propineb, fosetyl aluminum, sulfur, Bordeaux-mixture, copper-sulphate, copper-oxychloride, cuprous-oxide, copper-hydroxide, acibenzolar, metrafenone, pencycuron, 163 bethoxazin, diclomezine, fenpropidin, Phthalide, pyroquilon, spiroxamine, tricyclazole, triforine, cymoxanil, dodine, guazatine, iminoctadine, GY81330, NKI42650330, dicloran, dichlofluanid, tolylfluanid, zopfiellin, OK9601, fenaminosulf, oxolinic-acid, probenazole, bronopol, benclothiaz, methyl-bromide, methyl-iodide, metam, methyl-isothiocyanate, dazomet, DCIP, fosthiazate, cadusafos, fensulfothion, thionazin, fenamiphos, ethoprophos, dichlofenthion, isazofos, fosthietan, oxamyl, aldicarb, carbofuran, sulfuryl-fluoride, 1,3-dichloropropene, methyl 2,5-dichloroisonicotinate, or oryzaemate.

Preferably, the isothiazole oxime ether-containing strobilurin derivatives IV is present in the fungicidal composition in an amount between 1%-90% by mass percentage.

Preferably, the mass ratio of the isothiazole oxime ether-containing strobilurin derivatives IV to the above-described fungicide is from 1%:99% to 99%:1% by mass percentage.

Preferably, the formulation processed by the fungicidal composition is chosen from suspension concentrates for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent.

Preferably, the plant diseases controlled by the fungicidal composition are chosen from rice seedling blight, cotton rot, tomato root rot, potato late blight, tobacco black shank, millet powdery mildew, grape downy mildew, lettuce downy mildew, cucumber downy mildew, or cucumber anthracnose.

Preferably, the plant controlled by the fungicidal composition is chosen from rice, wheat, barley, oats, corn, sorghum, sweet potato, potato, tapioca, soybean, pea, broad bean, mung bean, adzuki bean, cotton, sericulture, peanut, rapeseed, sesame, sunflower, beet, sugar cane, coffee, cocoa, ginseng, fritillary, rubber, coconut, oil palm, sisal, tobacco, tomato, radish, cucumber, cabbage, celery, mustard, beet, rape, onions, garlic, watermelon, melon, cantaloupe, apple, citrus and peach, tea, wild vegetables, bamboo shoots, hops, pepper, banana, papaya, orchid, or bonsai.

Preferably, the isothiazole oxime ether-containing strobilurin derivatives IV can be used alone or can be mixed with one, two or more antiviral agents to form an antiviral mixture for agricultural and forestry and horticultural plant virus diseases controlling.

Preferably, the above-described antiviral agents are chosen from Benzothiadiazole, Tiadinil, abbreviated as TDL, thiazamide, SZG-7, 4-methyl-1,2,3-thiadiazole-5-carboxylic acid, 4-methyl-1,2,3-thiadiazol-5-formate, 4-methyl-1,2,3-thiadiazole-5-carboxylic acid ethyl ester, DL-β-aminobutyric acid, isotianil, 3,4-dichloroisothiazol-5-carboxylic acid, 3,4-dichloroisothiazol-5-formate, 3,4-dichloroisothiazol-5-carboxylic acid ethyl ester, ribavirin, Antofine, Ningnanmycin or salicylic acid, Cytosinpeptidemycin, methyl 2,5-dichloroisonicotinate, Oryzaemate, Validoxylamine A, or Validamycin.

Preferably, the isothiazole oxime ether-containing strobilurin derivatives IV is present in the antiviral composition in an amount between 1%-90% by mass percentage.

Preferably, the mass ratio of the isothiazole oxime ether-containing strobilurin derivatives IV to the above-described antiviral agents is from 1%:99% to 99%:1%.

Preferably, the formulation processed by the antiviral composition is chosen from suspension concentrates for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent.

Preferably, the plant viral diseases controlled by the antiviral composition are chosen from rice dwarf disease, yellow dwarf disease, stripe leaf blight, tomato fern leaf virus disease, pepper mosaic virus disease, tobacco vein necrosis virus disease, corn dwarf mosaic disease, cauliflower mosaic virus, citrus virus disease, orchid leaf virus, or Jianlan ring spot virus.

Preferably, the plants controlled by the antiviral composition are chosen from rice, wheat, barley, oats, corn, sorghum, sweet potato, potato, cassava, soybean, pea, broad bean, mung bean, adzuki bean, cotton, sericulture, peanuts, rapeseed, sesame, sunflower, beet, sugar cane, coffee, cocoa, ginseng, fritillary, rubber, coconut, oil palm, sisal, tobacco, tomato, radish, cucumber, cabbage, celery, mustard, beet, rape, onion, garlic, watermelon, melon, cantaloupe, apple, citrus and peach, tea, wild vegetables, bamboo shoots, hops, pepper, banana, papaya, orchid, or bonsai.

Preferably, the isothiazole oxime ether-containing strobilurin derivatives IV can be used alone or can be mixed with one, two or more acaricides to form a acaricide composition for controlling agricultural and forestry and horticultural plant diseases.

Preferably, the above-described acaricides are chosen from Azocyclotin, Cyhexatin, Fenbutatin oxide, Triphosphorustin, Chlorfenvinphos, Dimethylvinphos, Crotoxyphos, Dichlorvos, Heptenophos, Mevinphos, Monocrotophos, Dibrom, Chlorpyrifos, Pirimiphos ethyl, Dialifos, O,O-Dimethyl-S-methylcarbamoylmethyl phosphorothioate, Dioxathion, Ethion, Malathion, Methacrifos, Phosalone, Phoxim, Pirimiphos-methyl, Quinalphos, Sulfotep, Triazophos, Vamidothion, Isocarbophos, Methamidophos, Popetamphos, Phosmet, Arinathrin, Bifenthrin, Cyhalothrin, Gamma-Cyhalothrin, Fenpropathrin, Flucythrinate, Flumethrin, Tau-fluvalinate, brofluthrinate, Bifenazate, Fenothiocarb, Aldicarb, Butocarboxim, Oxamyl, Thiocarbonime, Thiofanox, Benomyl, Banol, Carbofuran, Carbosulfan, Metolcarb, promacyl, formetanate, N-2, 4-dimethylphenyl-N'-methylformamidine, Chlordimeform, Amitraz, Benzyl benzoate, Bromopropylate, Cyflumetofen, Acequinocyl, Flufenoxuron, Liuyangmycin, Piericidin, β-exotoxin, Tetranactin, Abamectin, Doramectin, Eprinomectin, Ivermectin, Selamectin, Moxidectin, pyrethrins, Nicotine, Matrine, Azadirachtin, rotenone, Tebufenpyrad, Pyridaben, Fenpyroximate, clofentezine, Propargite, Hexythiazox, Spirodiclofen, Fluacrypyrim, Ovex, or Pyridaben.

Preferably, the isothiazole oxime ether-containing strobilurin derivatives IV is present in the acaricidal composition in an amount between 1%-90% by mass percentage.

Preferably, the mass ratio of the isothiazole oxime ether-containing strobilurin derivatives IV to the above-described acaricidal agents is from 1%:99% to 99%:1%.

Preferably, the formulation processed by the acaricidal composition is chosen from seed treatment emulsion, water emulsion, microemulsion, suspoemulsion, capsule suspension, water-soluble granule, fine granule, soluble concentrate, poisonous valley, lumps Poison baits, granular baits, flake baits, concentrated baits, slow release blocks, electrostatic sprays, oil-in-water emulsions, smoke cans, smoke candles, smoke tubes, smoke sticks, smoke sheets, smoke pills, gas generators, ointments, Hot mist, cold spray, aerosol, solid/liquid mixed charge, liquid/liquid mixed charge, solid/solid mixed charge, lacquer, microparticle, trace powder, oil suspension, oil dispersible powder, thickener, pouring agent, seed coating agent, smear agent, film forming oil agent, ultra low volume liquid agent, or steam release agent.

Preferably, the mites controlled by the acaricidal composition are chosen from the genus *Aphididae*, the genus *Diptera*, the *eucalyptus*, the genus *Eucalyptus*, and the mites. World agricultural pests, forest pests, or horticultural pests and health hazardous pests.

Preferably, the plants controlled the acaricidal composition are chosen from rice, wheat, barley, oats, corn, sorghum, sweet potato, potato, tapioca, soybean, pea, broad bean, mung bean, adzuki bean, cotton, sericulture, peanuts, rapeseed, sesame, sunflower, beet, sugar cane, coffee, cocoa, ginseng, fritillary, rubber, coconut, oil palm, sisal, tobacco, tomato, radish, cucumber, cabbage, celery, mustard, beet, rape, onion, garlic, watermelon, melon, cantaloupe, apple, citrus and peach, tea, wild vegetables, bamboo shoots, hops, pepper, banana, papaya, orchid, or bonsai.

The biological activities of the isothiazole oxime ether-containing strobilurin derivatives IV of the present invention were evaluated as follows.

E. General Procedure for the Fungicide Activities of the Compounds IV:

A stock solution of each compound was prepared at 500 μg/mL using N,N-dimethylformamide (DMF) as a solvent. A working solution (50 μg/mL) was then prepared by diluting the stock solution (0.1 mL) with sterilized water (0.9 mL) in a 10 cm diameter Petri dish. Potato dextrose agar (PDA, 9 mL) was then added to prepare the plate. Before the plate solidification, the PDA was thoroughly mixed by turning around the Petri dish in the sterilized operation desk five times to scatter the compounds in PDA evenly. Then, 4 mm of diameter of fungi cake was inoculated on the plate and cultured in the culture tank at 24-26° C. The diameter of fungi spread was measured two days later. Growth inhibition was then calculated using the corresponding control. Fungi used in this study included *Alternaria solani, Botrytis cinerea, Rhizoctonia cerealis, Cercospora arachidicola, Pellicularia sasakii, Gibberella zeae, Sclerotinia sclerotiorum, Physalospora piricola*, and *Phytophthora infestans* (Mont) de Bary.

F. General Procedure for Systemic Acquired Resistance Screening of the Compounds IV:

In this assay, we used the tobacco against the TMV system. Direct antivirus activity was detected before its systemic acquired resistance determination. The in vitro activity of each compound against TMV was conducted using the conventional half-leaf juice robbing method: a fresh leaf of five to six leaves age of healthy tobacco that had been inoculated with TMV virus by the juice-leaf rubbing method was cut into two halves along the main vein. The concentration of TMV inoculation was $5.88 \times 10^{-2}$ μg/mL. The two halves were immersed into a solution of the test compound (500 μg/mL) and double-distilled water for 20 minutes, separately. The half-leaves were then cultured at 25° C. for 72 hours under the humidity of 100%, and the viral inflammations on the inoculated leaves were recorded. 2,4-dioxohexahydro-1,3,5-triazine (DHT) was used as a positive control. Three replicates were performed for each compound.

The in vitro inhibition ratio was calculated by comparing the average number of the viral inflammations on the two half-leaves according to eq 1. Determination of systemic acquired resistance activity of the tested compound against TMV was conducted according to the following procedures. Five pots of three to five leaves age of healthy whole tobacco plant were chosen for the screening of one compound. All fresh leaves were treated with 20 mL of a target compound (500 μg/mL) by spraying (leaf spray) or irrigation (soil treatment). The plants were then cultured in the green house for about seven days, after another new leaf was grown large enough for experiment in each pot; each newly grown leaf was inoculated by TMV ($5.88 \times 10^{-2}$ μg/mL) using the juice-leaf rubbing method. Double-distilled water, tiadinil, and BTH were sprayed (leaf spray) or irrigated (soil treatment) as CK and positive controls. Each inoculated tobacco plant was then placed at 25° C. for 72 hours of further cultivation; the viral inflammations on the inoculated leaves were recorded. The induction activity was evaluated using the antivirus inhibition ratio, which was calculated by the average number of the viral inflammations on the inoculated leaves with the corresponding control, according to eq 1.

$$R = \frac{CK - I}{CK} \times 100$$

Where R is the antivirus inhibition ratio (in vitro or induced in vivo) (%), CK is the average number of viral inflammations on the control half-leaf in vitro or each induced leave in vivo, and I is the average number of viral inflammations on the treatment half-leaf in vitro or each leaf induced in vivo.

The beneficial effects of the present invention are as follows: the isothiazolyl oxime ether strobilurin derivatives IV were optimized, and their fungicidal activities were evaluated.

The present invention more specifically describes synthesis, biological activities and applications of isothiazolyl oxime ether strobilurins derivative IV by specific examples, which are only used to specifically illustrate the present invention but not limit the present invention. In particular, biological activities of this invention include only an example, but are not limited to this invention. The specific implementations were as follows:

EXAMPLE 1

General Procedure for the Synthesis of Compounds II

A solution of compound I (1.10 mmol) in 15 ml ethanol was added to the solution of intermediates 3,4-dichloroisothiazole-5-substituted carbonyl compounds (1.02 mmol) in ethanol (15 ml), wherein 3,4-dichloroisothiazole-5-substituted carbonyl compounds are chosen from 3,4-dichloroisothiazole-5-carbaldehyde, 1-(3,4-dichloroisothiazol-5-yl)ethanone, and 4-(3,4-dichloroisothiazol-5-yl)but-3-en-2-one. And to the reaction mixture was added the catalytic amount of hydrochloric acid (2 mol/L) and stirred at room temperature overnight. The solvent was evaporated under reduced pressure and the residue was then purified by recrystallization in ethanol or column chromatography on silica gel using ethyl acetate and petroleum ether (b.p. 60-90° C.) with 1:9 of v/v as an eluent to obtain II in a 70-80% yield; Wherein $R^1$ is methyl; Y is $(CH=CH)_m$, m=0; Z is N, $^1H$ NMR (CDCl$_3$) δ 7.51 (s, 1H, Ph-H), 7.47-7.43 (m, 2H, Ph-H), 7.24-7.20 (m, 1H, Ph-H), 5.23 (s, 2H, Ph-CH$_2$), 4.06 (s, 3H, O—CH$_3$), 3.83 (s, 3H, O—CH$_3$), 2.52 (s, 3H, N=C—CH$_3$). The amount of compound II preparation and the volume of the reaction vessel increase or decrease in corresponding proportions. The yields, physical properties, $^1H$ NMR data of the compounds II are listed in Table 1.

EXAMPLE 2

General Procedure for the Synthesis of the Other Compounds II

A solution of compounds I (1.10 mmol) in 15 ml ethanol was added to the solution of commercially available 3,4-dichloroisothiazole-5-carbonitrile (1.00 mmol) in ethanol (15 ml), 2-mercapoacetic acid (0.10 g, 1.09 mmol) was added to the reaction mixture for stirring at room temperature overnight. The solvent was evaporated under reduced pressure and the residue was then purified by recrystallization in ethyl acetate or column chromatography on silica gel using ethyl acetate and petroleum ether (b.p. 60-90° C.) with 1:10 of v/v as an eluent to give II in a 80-97% yield. Wherein $R^1$ is amino; Y is $(CH=CH)_m$, m=0; Z is N, $^1H$ NMR (CDCl$_3$) δ 7.40-7.30 (m, 3H, Ph-H), 7.13 (d, J=6.4 Hz, 1H, Ph-H), 5.18 (s, 2H, NH$_2$), 4.91 (s, 2H, Ph-CH$_2$), 3.97 (s, 3H, O—CH$_3$), 3.79 (s, 3H, O—CH$_3$) The yields, physical properties, $^1H$ NMR data of the compounds II are listed in Table 1.

EXAMPLE 3

General Procedure for the Synthesis of the Other Compounds III

One of intermediates II (2.49 mmol) was dissolved in 15 ml methanol, the solution of sodium hydroxide (0.30 g, 7.47 mmol) in 15 ml methanol was added to the reaction mixture for 30 minutes of refluxing. After completing of the reaction, the solvent was evaporated under reduced pressure and to the residue was added 15 ml water. The aqueous phase was adjusted to pH 2-3 with dilute hydrochloric acid (3 mol/L). The aqueous layer was extracted with ethyl acetate (2×15 ml). The organic layers were combined and washed with saturated brine (50 ml), dried over sodium sulfate. After filtration, the solvent was evaporated to obtain the compounds III as a white solid in a 95% yield.

EXAMPLE 4

General Procedure for the Synthesis of the Other Compounds IV

The reaction mixture of the compound III (0.75 mmol), EDCI (0.17 g, 0.90 mmol), HOBT (0.11 g, 0.77 mmol) in dichloromethane (25 ml) was stirred for 15 minutes in ice bath. A solution of amine in dichloromethane (25 ml) was added and followed by Et$_3$N (0.09 g, 0.90 mmol), the reaction mixture was stirred for further 16 hours. After completion of the reaction, the organic layer was successively washed with water (2×30 ml) and saturated brine (40 ml), dried over MgSO$_4$ and concentrated under vacuum. After filtration, the solvent was evaporated. The residue was then purified by column chromatography on silica gel using ethyl acetate and petroleum ether (60-90° C.) with 1:4 of v/v as an eluent to give a white solid IV in a 95% yield. The yields, physical properties, $^1H$ NMR data of the compounds IV are listed in Table 1.

EXAMPLE 5

General Procedure for the Synthesis of the Other Compound CL04-00

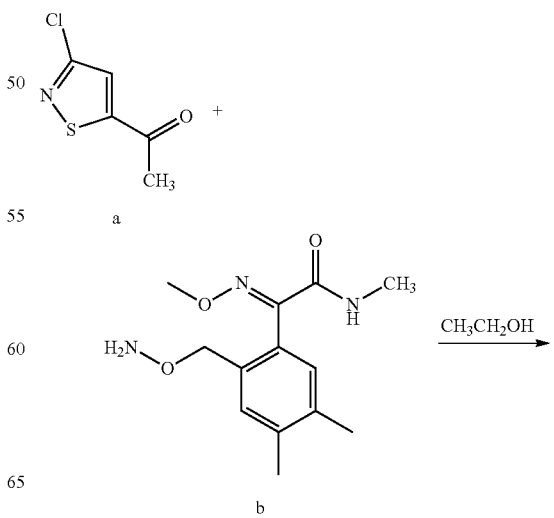

-continued

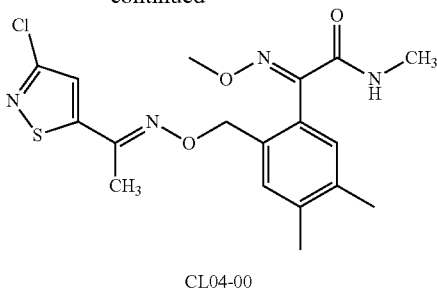

CL04-00

A solution of compounds b (1.10 mmol) in 15 ml ethanol was added to the solution of commercially available 1-(3-chloroisothiazol-5-yl)ethanone a (1.00 mmol) in ethanol (15 ml), and the reaction mixture was added the catalytic amount of hydrochloric acid (2 mol/L) and stirred at room temperature for overnight. The solvent was evaporated under reduced pressure and the residue was then purified by recrystallization in ethanol or column chromatography on silica gel using ethyl acetate and petroleum ether (b.p. 60-90° C.) with 1:4 of v/v as an eluent to obtain II in a 68.22% yield.

EXAMPLE 6

General Procedure for the Synthesis of the Other Compound CL05-00

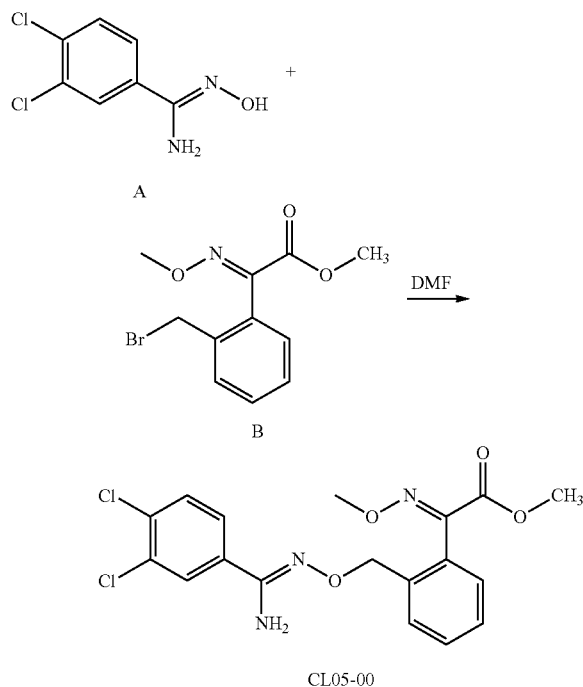

In order to compare the difference activities between the compounds CL05-00 whose structure is closest to the structure of the compound in the present invention, the compound CL05-00 was synthesized according to the literature. The steps are described as follows:

The reaction mixture of the compound A (1.00 mmol) in 15 ml DMF and CsCO$_3$ (1.50 mmol) was stirred for 5 minutes. The compound B was added to a solution and was stirred at room temperature for 12 hours. The solvent was evaporated under reduced pressure and the residue was then purified by recrystallization in ethanol or column chromatography on silica gel using ethyl acetate and petroleum ether (b.p. 60-90° C.) with 1:8 of v/v as an eluent to obtain CL05-00 in a 55.57% yield.

EXAMPLE 7

Results of the Fungicide Activities of the Compounds IV

It is worth noting that the compound CL04-00 reported in the patent WO 2000/003974 A1 is closest to the structure of the compound in the present invention. In order to compare the biological activity of the novel compound synthesized by the present invention, the present invention synthesizes the compound CL04-00.

The results of the fungicide activities of the compounds IV at 50 µg/mL are listed in Table 2. It showed that all compounds in the present invention have different potential of fungicidal activity. The compounds CL03-49, CL03-50, CL04-03, CL04-04-A, CL04-04-B, CL04-06, CL04-15A, CL04-15B, CL04-15C, CL04-22A, CL04-22D, CL04-25C, CL04-17, CL04-32A, CL04-32B, CL04-32C and CL04-32D showed over 30% inhibition against *A. solani* at 50 µg/mL, which showed over 10% better inhibition than that of the compound CL04-00; and among them, the compounds CL03-50, CL04-03, CL04-04-A, CL04-06, CL04-15B, CL04-15C and CL04-32D showed over 10% better inhibition than that of the compound CL05-00, besides, the compounds CL04-04-A and CL04-15B showed more than 80% inhibition against *A. solani*, which showed over 10% and 30% higher inhibition than that of the positive controls azoxystrobin and kresoxim-methyl respectively; especially CL04-15B displayed the best fungicidal activity, up to 100%. The compounds CL03-49, CL03-50, CL04-04-A, CL04-04-B, CL04-06, CL04-15A, CL04-15B, CL04-15C, CL04-22A, CL04-22B, CL04-22C, CL04-22D, CL04-22E, CL04-25C, CL04-17, CL04-32A, CL04-32B, CL04-32C and CL04-32D showed over 30% inhibition against *C. arachidicola* at 50 µg/mL, which over 10% better inhibition than that of the compound CL04-00; and among them, the compounds CL04-04-A, CL04-04-B, CL04-15B, CL04-15C, CL04-22D and CL04-32D showed more than 75% inhibition, which showed over 10% better inhibition than that of the compound CL05-00, and over 20% better than that of the positive controls azoxystrobin and kresoxim-methyl; and the compounds CL04-03 and CL04-15B exhibited 100% and 91.67%, respectively. The compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-22E, CL04-22F, CL04-24, CL04-25A, CL04-25B, CL04-25C, CL04-25E, CL04-17, CL04-32A, CL04-32B, CL04-32C, CL04-32D and CL04-32F showed over 30% inhibition against *G. zeae* at 50 µg/mL, which showed over 10% better inhibition than that of the compound CL04-00 and kresoxim-methyl; and among them, the compounds CL04-03, CL04-04-A, CL04-04-B, CL04-06, CL04-15B, CL04-15C, CL04-22A, CL04-22B, CL04-22C, CL04-22D, CL04-25B, CL04-25C, CL04-17, CL04-32B, CL04-32C and CL04-32F showed over 10% better inhibition than that of the compound CL05-00; and among them, CL04-15C, CL04-22B, CL04-22D, CL04-25C, CL04-32B and CL04-32D showed more than 80% inhibition, which showed over 10% better than that of the positive control azoxystrobin; especially the compounds CL04-22B, CL04-22D, CL04-25C and CL04-32D showed the best fungicidal activity, up to 100%. The compounds CL03-49, CL03-50, CL04-03, CL04-04-A, CL04-04-B, CL04-06, CL04-15A, CL04-15B, CL04-15C, CL04-22B, CL04-22C, CL04-22D, CL04-17, CL04-32B, CL04-32C and CL04-32D showed over 45% inhibition against P. piricola at 50 μg/mL, which showed over 10% better inhibition than that of the compound CL04-00; and among them, the compounds CL03-49, CL03-50, CL04-03, CL04-04-A, CL04-06, CL04-15C, CL04-22D, CL04-32C showed more than 70% inhibition, which showed over 10% better inhibition than that of the compound CL05-00 and kresoxim-methyl; and the compound CL04-03 exhibited the best inhibition, up to 86.96%. The compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-22E, CL04-22F, CL04-25C, CL04-17, CL04-32A, CL04-32B, CL04-32C and CL04-32D showed over 45% inhibition against B. cinerea at 50 μg/mL, which showed over 10% better inhibition than that of the compound CL04-00; and among them, the compounds CL03-49, CL03-50, CL04-03, CL04-04-A, CL04-04-B, CL04-06, CL04-15A, CL04-15B, CL04-15C, CL04-22D and CL04-22E showed over 10% better inhibition than that of kresoxim-methyl; and the compounds CL03-49, CL03-50, CL04-03, CL04-04-A, CL04-06, CL04-15A, CL04-15B, CL04-15C, CL04-22D and CL04-17 showed 100% inhibition, which showed over 25% better inhibition than that of the compound CL05-00 and higher than azoxystrobin. The compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-22F, CL04-25A, CL04-25B, CL04-25C, CL04-25D, CL04-25E, CL04-17, CL04-32A, CL04-32B, CL04-32C, CL04-32D and CL04-32F showed over 40% inhibition against S. sclerotiorum at 50 μg/mL, which showed over 10% better inhibition than that of the compound CL04-00; and among them, the compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-25C, CL04-17, CL04-32B, CL04-32C and CL04-32D showed over 10% better inhibition than that of kresoxim-methyl; besides, the compounds CL04-03, CL04-04-A, CL04-06, CL04-15A, CL04-15B, CL04-15C, CL04-22B, CL04-22D showed over 90% inhibition, which showed over 20% better inhibition than that of the compound CL05-00 and higher than azoxystrobin; especially CL04-03, CL04-06, CL04-15A, CL04-22B, CL04-22D showed the best fungicidal activity, up to 100%. The compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-22E, CL04-22F, CL04-24, CL04-25A, CL04-25B, CL04-25C, CL04-25E, CL04-17, CL04-32A, CL04-32B, CL04-32C, CL04-32D and CL04-32F showed over 50% inhibition against R. cerealis at 50 μg/mL, which showed over 40% better inhibition than that of the compound CL04-00; and among them, the compounds CL03-49, CL03-50, CL04-03, CL04-04-A, CL04-06, CL04-15B, CL04-22D, CL04-25C and CL04-32B showed over 90% inhibition, which showed over 10% better inhibition than that of the compound CL05-00 and azoystrobin, and over 20% higher inhibition than that of kresoxim-methyl. The compounds CL03-49, CL03-50, CL04-03, CL04-04-A and CL04-06 showed the best fungicidal activity, up to 100%. The compounds CL03-49, CL03-50, CL04-03, CL04-04-A, CL04-04-B, CL04-06, CL04-15A, CL04-15B, CL04-15C, CL04-22B, CL04-22C, CL04-22B, CL04-25A, CL04-25C, CL04-17, CL04-32A, CL04-32B, CL04-32C and CL04-32D showed over 35% inhibition against P. sasakii at 50 μg/mL, which showed over 10% better inhibition than that of the compound CL04-00; and among them, the compounds CL04-06, CL04-15A, CL04-15B, CL04-15C, CL04-22B, CL04-22D, CL04-25C, CL04-32B, CL04-32C and CL04-32D showed over 10% better inhibition than that of the compound CL05-00 and kresoxim-methyl; besides the compounds CL04-22D, CL04-25C and CL04-32D showed over 80% inhibition, which showed better inhibition than that of azoxystrobin. The compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-25A, CL04-25C, CL04-17, CL04-32A, CL04-32B, CL04-32C and CL04-32D showed over 40% inhibition against P. infestans (Mont.) de Bary at 50 μg/mL, which showed over 10% better inhibition than that of the compound CL04-00 and kresoxim-methyl, and among them, the compounds CL04-03, CL04-04-B, CL04-06, CL04-15A, CL04-15B, CL04-15C, CL04-22A, CL04-22B, CL04-22C, CL04-22D, CL04-25A, CL04-25C, CL04-32A, CL04-32B, CL04-32C and CL04-32D showed over 55% inhibition, which showed over 10% better inhibition than that of azoxystrobin; besides, the compounds CL04-15B, CL04-15C, CL04-22C, CL04-22D, CL04-25A, CL04-25C, CL04-32A, CL04-32B, CL04-32C and CL04-32D showed over 86% inhibition, which showed over 10% better inhibition than that of the compound CL05-00; especially the compounds CL04-22C, CL04-22D, CL04-25A, CL04-25C, CL04-32B, CL04-32C and CL04-32D showed the best fungicidal activity, up to 100%. In summary, the compounds CL04-03, CL04-15B, CL04-15C and CL04-22D showed broad spectrum of fungicidal activities.

EXAMPLE 8

Fungicidal Efficacy of the Compounds IV in the Present Invention Against *Sphaerotheca fuliginea*

Fungicidal efficacy of the active compound in field was carried out in the present invention. The name and code of the selected control object was *Sphaerotheca fuliginea*. is "Jinyou 40" cucumber was selected as test crop variety. Application method and water consumption (L/ha): Spraying is applied before or at the onset of the disease. Spray the plants evenly with a dose of 675 L/hm$^2$, and spray the same amount of water as a blank control. The results are listed in Table 3, and it showed that fungicidal efficacy of a 9.60% EC of CL04-22D against *S. fuliginea* was 78.62%; while efficacy of 250 g/L azoxystrobin SC and 250 g/L pyraclostrobin EC were 70.19% and 68.02%, respectively. The structure of trifloxystrobin is closest to the structure of the compound in the present invention, and efficacy of CL04-22D displayed over 10% higher than this positive control. By using analysis of variance and multiple comparisons, 9.60% CL04-22D EC showed significantly better efficacy against *S. fuliginea* than 250 g/L azoxystrobin SC and 50% trifloxystrobin WG at an application dosage of 37.5 g ai/ha. During the test, every treatment of 9.60% CL04-22D EC have no adverse effects on cucumbers. In summary, 9.60% CL04-22D EC showed good efficacy against *S. fuliginea* on cucumber.

EXAMPLE 9

Fungicidal Efficacy of the Compounds IV in the Present Invention Against *Pseudoperonspera cubensis*

Fungicidal efficacy of active compound in field was carried out in the present invention. The name and code of the selected control object was *Pseudoperonspera cubensis*. "Jinyou 3" cucumber was selected as test crop variety. Application method and water consumption (L/ha): Spraying is applied before or at the onset of the disease. Spray the plants evenly with a dose of 675 L/hm$^2$, and spray the same amount of water as a blank control. The results are listed in Table 4, and it showed that fungicidal efficacy of a 9.60% EC of CL04-22D against *P. cubensis* was 79.18%; which showed 5% efficacy higher than 50% trifloxystrobin WG (72.02%); and was similar to 250 g/L pyraclostrobin EC (77.52%). By using analysis of variance and multiple comparisons, 9.60% CL04-22D EC showed similar efficacy against *P. cubensis* to 250 g/L pyraclostrobin EC and significantly better efficacy 50% trifloxystrobin WG at an application dosage of 75 g ai/ha. During the test, every treatment of 9.60% CL04-22D EC have no adverse effects on cucumbers. In summary, 9.60% CL04-22D EC showed good efficacy against *P. cubensis* on cucumber.

EXAMPLE 10

General Procedure for Systemic Acquired Resistance Screening of the Compounds IV The results of activity screening against TMV are listed in Table 5, and it indicated that most compounds showed a certain degree of direct inhibition activities against TMV at 100 µg/mL. In curative mode, the compounds CL03-49, CL04-50, CL04-03, CL04-25A, CL04-25D, CL04-17, CL04-32B and CL04-32F had over 30% inhibition activities against TMV; among them, the compounds CL03-49, CL04-50, CL04-03, CL04-25A, CL04-32B and CL04-32F showed over 10% inhibition higher than that of the compounds CL04-00, CL05-00 and Isotianil; and the compounds CL04-25A, CL04-32B and CL04-32F had over 60% inhibition against TMV, especially the compounds CL04-25A and CL04-32B showed higher inhibition against TMV than Ningnanmycin. In inactivation mode, the compounds CL03-49, CL03-50, CL04-03, CL04-04-A, CL04-04-B, CL04-15A, CL04-15B, CL04-15C, CL04-22A, CL04-22B, CL04-22E, CL04-17, CL04-32A, CL04-32B, CL04-32C and CL04-32D had over 30% inhibition activities against TMV, which showed over 10% inhibition higher than that of the compounds CL04-00, CL05-00 and Isotianil; especially the compounds CL03-50, CL04-04-A and CL04-32B had over 70% inhibition against TMV, which were similar to Ribavirin. And the compound CL04-03 showed the best inactivation inhibition, up to 80%. In protection mode, the compounds CL03-50, CL04-04-A, CL04-04-B, CL04-06, CL04-15A, CL04-22B, CL04-22D, CL04-25A, CL04-25C, CL04-32A, CL04-32E and CL04-32F had over 40% inhibition against TMV, which showed over 10% inhibition higher than that of the compounds CL04-00, CL05-00 and Isotianil; among them, the compounds CL03-50, CL04-04-A, CL04-06, CL04-22B, CL04-25C and CL04-32F had over 50% inhibition against TMV. In induction mode, the compounds CL03-49, CL03-50, CL04-03, CL04-04-A, CL04-04-B, CL04-06, CL04-15A, CL04-15B, CL04-15C, CL04-22A, CL04-22B, CL04-22C, CL04-22D, CL04-22F, CL04-24, CL04-25A, CL04-25C, CL04-17, CL04-32A, CL04-32B, CL04-32D and CL04-32F had over 30% inhibition against TMV, which showed over 10% inhibition higher than that of the compounds CL04-00 and CL05-00; among them, the compounds CL03-49, CL03-50, CL04-03, CL04-04-A, CL04-06, CL04-15A, CL04-15B, CL04-15C, CL04-22C, CL04-22D, CL04-25A, CL04-32B, CL04-32E had over 70% inhibition against TMV, especially the compounds CL03-50, CL04-15C, CL04-22C had over 80% induction inhibition against TMV, which showed higher inhibition than that of TDL, BTH, SZG-7 and Isotianil. In inactivation mode, the above compounds showed good inactivation activity. In summary, the compounds CL04-04-A and CL04-32B showed good inhibition against TMV. The most compounds in the present invention had good inhibition against TMV.

The isothiazole oxime ether strobilurins derivatives IV of the present invention is also resistant to rice dwarf disease, yellow dwarf disease, stripe leaf blight, tomato fern leaf virus disease, pepper mosaic virus disease, tobacco vein necrosis virus, corn Dwarf mosaic disease, cauliflower mosaic virus, citrus virus disease, broccoli virus disease, Jianlan ring spot virus agriculture and forestry, and horticultural plant virus diseases have good antiviral activity.

EXAMPLE 11

The Use of the Isothiazole Oxime Ether-Containing Strobilurin Derivatives IV of the Present Invention in Combination with an Insecticide for Controlling Agricultural and Forestry and Horticultural Plant Pests The isothiazole oxime ether-containing strobilurin derivatives IV of this invention is combined with one, two or more insecticides to form an insecticidal composition for agricultural, forestry and horticultural plant pests controlling. The insecticides are chosen from Chlorpyrifos, Diazinon, Acetamiprid, Emamectin, Milbemectin, Abamectin, Spinosad, Fenvalerate, S-fenvalerate, θ-Cypermethrin, β-Cypermethrin, Cyhalothrin, Deltamethrin, β-Cyfluthrin, λ-Cyhalothrin, Permethrin, S-Bioallethrin, Bifenthrin, Ethofenprox, Tau-fluvalinate, Imidacloprid, Nitenpyram, Imidaclothiz, Thiacloprid, Thiamethoxam, Clothianidin, Dinotefuran, Diflubenzuron, chlorbenzuron, Teflubenzuron, Hexaflumuron, Flufenoxuron, Chlorfluazuron, Lufenuron, Penfluoron, Noviflumuron (CAS: 121451-02-3), Flucycloxuron, Novaluron, Bay sir 6874, Bay SIR-8514, N-[[5-(4-bromophenyl)-6-methyl pyrazin-2-yl]carbamoyl]-2-chlorobenzamide, Bistrifluron, (CAS: 467427-81-1), Tebufenozide, Halofenozide, Methoxyfenozide, Chromafenozide, Dimethoate, O,O-Dimethyl-S-methyl carbamoylmethyl phosphorothioate, Dichlorvos, Orthene, Triazophos, Quinalphos, Pyridaphenthion, Isazophos, Isoprocarb, Carbaryl, Pirimicarb, Metolcarb, Cartap, Fenobucarb, N-methyl-2,3-dimethylphenyl carbamate, Benfuracarb, Carbosulfan, Bromopropylate, Hexythiazox, Fenpyroximate, Pyridaben, Clofentezine, Propargite, Diafenthiuron, Pymetrozine, Spirodiclofen, Spirotetramatr, flufiprole, Azocyclotin, Buprofezin, Mocap, Fipronil, Molosultap, Chloantraniliprole, Flubendiamide, Cyhalodiamide, Cyantraniliprole, Tolfenpyrad, Chlorfenapyr, Etoxazole, 4-Chloro-N-(4-tert-butyl benzyl)-3-ethyl-1-methyl-1H-pyrazole-5-carboxamide (CAS: 119168-77-3), Tebufenpyrad, 4-chloro-5-[(6-chloropyridin-3-yl)methoxy]-2-(3,4-dichlorophenyl)pyridazin-3-one (CAS: 107360-34-9), and Pyriproxyfen. The isothiazole oxime ether-containing strobilurin derivatives IV is present in the insecticidal composition in an amount between 1%-90% by mass percentage. The mass ratio of the isothiazole oxime ether-containing strobilurin derivatives IV to the above-described insecticide is from 1%:99% to 99%:1%. The plant pests controlled by the insecticidal composition are chosen from *Tetranychus cinnbarinus, Locusta migratoria manilensis*, cypress locust, rice blast, Japanese yellow ridge, single locust, oriental carp, rice locust, scorpion horse, greenhouse hummer, rice tube hummer, wheat tube hummer, greenhouse whitefly, whitefly, black-tailed leafhopper, big green leafhopper, cotton leafhopper, spotted wax hopper, brown plant hopper, white-backed plant hopper, gray plant hopper, sugarcane, squared cornucopia, cotton aphid, wheat fork, wheat long tube, sorghum, radish, blown sorghum, mulberry scorpion, scorpion shield, pear round scorpion, white wax worm, red wax scorpion, Korean ball scorpion, *stephanitis nashi esaki* et *takeya*, banana nets, fine-horned flower buds, tiny flower buds, needle-edge mites, rice spider mites, rice brown mites, rice black mites, rice green mites, green blind mites, ticks, black scorpions, large grass mites, licao, chinese grasshopper, moth, yellow moth, brown moth, flat moth, wheat moth, cotton bollworm, sweet potato moth, diamondback moth, peach small heartworm, soybean heartworm, peach small carnivorous worm, apple leaf roller moth, brown leaf moth, yellow leaf moth, sorghum, pea pod, corn borer, stem borer, rapeseed meal, rice leaf roller, stripe, roller leafhopper, armyworm, *Spodoptera litura*, cotton small bridge worm, beet armyworm, giant salamander, dingdian diamond, small tiger, earth tiger, yellow tiger, toxic moth, gypsy moth, sweet potato hawk moth, bean hawk moth, straight grain rice butterfly, cryptic valley butterfly, citrus phoenix butterfly, jade belt phoenix butterfly, cabbage butterfly, ramie red butterfly, ramie butterfly, bean phthalocyanine, venus carapace, wrinkle-skinned armor, wheat-spotted armor, ditch-gold needle, fine-necked Golden Needle, *G. striata*, Black-skinned scorpion, citrus small jiding, lampra limbata gebler, *Tenebrio molitor*, Black mealworm, *tribolium castaneum* herbst, *Tribolium confusum* jac. du val., patina, golden tortoise, dark golden tortoise, north China black scorpion golden tortoise, mulberry ox, star celestial, orange brown hornbill, peach red neck horn, big worm leaf worm, small cockroach leaf worm, yellow squash, yellow scalloped beetle, mung bean elephant, pea elephant, broad bean elephant, corn elephant, rice elephant, Dolerus Chu, pear fruit sawfly, yellow belt wasp, armyworm white star wasp, Chrysalis suspense, *Campoletis chlorideae* Uchida, *Verruca verruca*, mosquito, fly, horsefly, wheat blossom midge, wheat midge, rice gall midge, Tetradacus *citri*, melon fruit fly, wheat fly ash, Leafminer, soybean stem borer, wheat straw flies, seed fly, onion fly, carrot fly, *Exorista civilis* Rondani, and Mailing flies of corn borer. The plant controlled by the pesticidal composition is selected from the group consisting of rice, wheat, barley, oats, corn, sorghum, sweet potato, potato, tapioca, soybean, pea, broad bean, mung bean, adzuki bean, cotton, sericulture, peanut, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, rape, onions, garlic, watermelon, melon, cantaloupe, papaya, apple, citrus and peach, tea, wild vegetables, bamboo shoots, hops, banana, orchid, or bonsai.

EXAMPLE 12

The Use of the Isothiazole Oxime Ether-Containing Strobilurin Derivatives IV of the Present Invention in Combination with a Fungicide for Controlling Agricultural and Forestry and Horticultural Plant Diseases The isothiazole oxime ether-containing strobilurin derivatives IV of the present invention is combined with one, two or more fungicides to form a fungicidal composition for controlling agricultural and forestry and horticultural plant diseases. The above-described fungicides are chosen from Benzothiadiazole, Tiadinil, abbreviated as TDL, thiazamide, SZG-7, 4-methyl-1,2,3-thiadiazole-5-carboxylic acid, 4-methyl-1,2,3-thiadiazol-5-formate, 4-methyl-1,2,3-thiadiazole-5-carboxylic acid ethyl ester, DL-β-aminobutyric acid, isotianil, 3,4-dichloroisothiazol-5-carboxylic acid, 3,4-dichloroisothiazol-5-formate, 3,4-dichloroisothiazol-5-carboxylic acid ethyl ester, ribavirin, Antofine, Ningnanmycin or salicylic acid, cymoxanil, thiram, Zinc bis dimethyldithiocarbamate, mancozeb, ethylphosphorus, Thiophanate-methyl, chlorothalonil, Fenaminosulf, procymidone, fenpropidin, Thiophanate-methyl, thiophanate, Metalaxyl-M, flumorph, Dimethomorph, benalaxylM, diclocymet, flusulfamide, TF-991, thifluzamide, flutolanil, tecloftalam, carpropamid, cyflufenamid, fenhexamide, fenoxanil, silthiopham, furametpyr, penthiopyrad, mandipropamid, zoxamide, fenfuram, carboxin, chlozolinate, iprodione, procymidone, azoxystrobin, dimoxystrobin, fluoxastrobin, kresoxim-methyl, metominostrobin, orysastrobin, picoxystrobin, pyraclostrobin, trifloxystrobin, enestroburin, SYP-1620, Azaconazole, bromuconazole, cyproconazole, difenoconazole, diniconazole, diniconazoleM, epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimenol, triticonazole, bitertanol, thiabendazole, fuberidazole, imazalil, S-imazalil, prochloraz, triflumizole, cyazofamid, fenamidone, oxpoconazole, pefurazoate, famoxadone, SYPZ048, hymexazol, oxadixyl, ethaboxam, etridiazole, octhilinone, benthiazole, dodemorph, fenpropimorph, tridemorph, fenpiclonil, fludioxonil, fluazinam, pyrifenox, ICIA0858, boscalid, fluopicolide, PEIP, cyprodinil, diflumetorim, ferimzone, mepanipyrim, pyrimethanil, fenarimol, nuarimol, chinomethionat, dithianon, ethoxyquin, 8 hydroxyquinoline, sulfate, proquinazid, quinoxyfen, diethofencarb, iprovalicarb, benthiavalicarb, Isopropyl, propamocarb, methasulfocarb, edifenphos, iprobenfos, pyrazophos, tolclofosmethyl, S-blasticidin, Kasugamycin, myxothiazol, polyoxins, olyoxorim, pseudomycin, PSFD271, validamycin, jinggangmycin, streptomycin, metalaxyl, furalaxyl, benalaxyl, ofurace, mepronil, carbendazim, benomyl, thiophanate-methyl, triadimefon, bupirimate, dimethirimol, ethirimol, captafol, captan, folpet, vinclozolin, fluoroimide, dimethachlon, isoprothiolane, EBP, bismerthiazol, quintozene, propineb, fosetylaluminium, sulfur, Bordeaux-mixture, copper-sulphate, copper-oxychloride, cuprous-oxide, copper-hydroxide, acibenzolar, metrafenone, pencycuron, bethoxazin, diclomezine, fenpropidin, Phthalide, pyroquilon, spiroxamine, tricyclazole, triforine, cymoxanil, dodine, guazatine, iminoctadine, GY81330, NKI42650330, dicloran, dichlofluanid, tolylfluanid, zopfiellin, OK9601, fenaminosulf, oxolinic-acid, probenazole, bronopol, benclothiaz, methyl-bromide, methyl-iodide, metam, methyl-isothiocyanate, dazomet, DCIP, fosthiazate, cadusafos, fensulfothion, thionazin, fenamiphos, ethoprophos, dichlofenthion, isazofos, fosthietan, oxamyl, aldicarb, carbofuran, sulfuryl-fluoride, 1,3-dichloropropene, methyl 2,5-dichloroisonicotinate, or oryzaemate.

The isothiazole oxime ether-containing strobilurin derivatives IV is present in the fungicidal composition in an amount between 1%-90% by mass percentage. The mass ratio of the isothiazole oxime ether-containing strobilurin derivatives IV to the above-described fungicide is from 1%:99% to 99%:1%. The formulation processed by the fungicidal composition is chosen from suspension concentrates for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent. The plant disease controlled by the fungicidal composition is selected from the group consisting of rice seedling cotton rot, tomato root rot, potato late blight, tobacco black shank, millet powdery mildew, grape downy mildew, lettuce downy mildew, cucumber Downy mildew, and cucumber anthracnose. The plant controlled by the fungicidal composition is chosen from rice, wheat, barley, oats, corn, sorghum, sweet potato, potato, cassava, soybean, pea, broad bean, mung bean, adzuki bean, cotton, sericulture, peanut, rape, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, onion, garlic, watermelon, melon, cantaloupe, apple, citrus and peach, tea, wild vegetables, bamboo shoots, hops, banana, papaya, orchid, or bonsai.

EXAMPLE 13

The Use of the Isothiazole Oxime Ether-Containing Strobilurin Derivatives IV of the Present Invention in Combination with an Anti-Plant Virus Agent for Controlling Agricultural and Forestry and Horticultural Plant Diseases The isothiazole oxime ether-containing strobilurin derivatives IV can be used alone or can be mixed with one, two or more antiviral agents to form an antiviral mixture for controlling agricultural and forestry and horticultural plant virus diseases. The above-described antiviral agents are chosen from Benzothiadiazole, Tiadinil, abbreviated as TDL, thiazamide, SZG-7, 4-methyl-1,2,3-thiadiazole-5-carboxylic acid, 4-methyl-1,2,3-thiadiazol-5-formate, 4-methyl-1,2,3-thiadiazole-5-carboxylic acid ethyl ester, DL-β-aminobutyric acid, isotianil, 3,4-dichloroisothiazol-5-carboxylic acid, 3,4-dichloroisothiazol-5-formate, 3,4-dichloroisothiazol-5-carboxylic acid ethyl ester, ribavirin, Antofine, Ningnanmycin or salicylic acid, Cytosinpeptidemycin, methyl 2,5-dichloroisonicotinate, Oryzaemate, Validoxylamine A, or Validamycin. The isothiazole oxime ether-containing strobilurin derivatives IV is present in the antiviral composition in an amount between 1%-90% by mass percentage. The mass ratio of the isothiazole oxime ether-containing strobilurin derivatives IV to the above-described antiviral agents is from 1%:99% to 99%:1%. The formulation processed by the antiviral composition is chosen from suspension concentrates for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent. The plants viral diseases controlled by the antiviral composition are chosen from rice dwarf disease, yellow dwarf disease, stripe leaf blight, tomato fern leaf virus disease, pepper mosaic virus disease, tobacco vein necrosis virus disease, corn dwarf mosaic disease, cauliflower mosaic virus, citrus virus disease, orchid leaf virus, or Jianlan ring spot virus. The plants controlled by the antiviral composition are chosen from rice, wheat, barley, oats, corn, sorghum, sweet potato, potato, cassava, soybean, pea, broad bean, mung bean, adzuki bean, cotton, sericulture, peanuts, rapeseed, sesame, sunflower, beet, sugar cane, coffee, cocoa, ginseng, fritillary, rubber, coconut, oil palm, sisal, tobacco, tomato, radish, cucumber, cabbage, celery, mustard, beet, rape, onion, garlic, watermelon, melon, cantaloupe, papaya, apple, citrus and peach, tea, wild vegetables, bamboo shoots, hops, pepper, banana, orchid, or bonsai.

EXAMPLE 14

The Use of the Isothiazole Oxime Ether-Containing Strobilurin Derivatives IV of the Present Invention in Combination with an Acaricide for Controlling Agricultural and Forestry and Horticultural Plant Damage The isothiazole oxime ether-containing strobilurin derivatives IV can be used alone or can be mixed with one, two or more acaricides to form an acaricide composition for controlling agricultural and forestry and horticultural plant diseases. The above-described acaricides are chosen from Azocyclotin, Cyhexatin, Fenbutatin oxide, Triphosphorustin, Chlorfenvinphos, Dimethylvinphos, Crotoxyphos, Dichlorvos, Heptenophos, Mevinphos, Monocrotophos, Dibrom, Chlorpyrifos, Pirimiphos ethyl, Dialifos, O,O-Dimethyl-S-methylcarbamoylmethyl phosphorothioate, Dioxathion, Ethion, Malathion, Methacrifos, Phosalone, Phoxim, Pirimiphos-methyl, Quinalphos, Sulfotep, Triazophos, Vamidothion, Isocarbophos, Methamidophos, Popetamphos, Phosmet, Arinathrin, Bifenthrin, Cyhalothrin, Gamma-Cyhalothrin, Fenpropathrin, Flucythrinate, Flumethrin, Tau-fluvalinate, brofluthrinate, Bifenazate, Fenothiocarb, Aldicarb, Butocarboxim, Oxamyl, Thiocarbonime, Thiofanox, Benomyl, Banol, Carbofuran, Carbosulfan, Metolcarb, promacyl, formetanate, N-2,4-dimethylphenyl-N'-methylformamidine, Chlordimeform, Amitraz, Benzyl benzoate, Bromopropylate, Cyflumetofen, Acequinocyl, Flufenoxuron, liuyangmycin, piericidin, β-exotoxin, tetranactin, Abamectin, Doramectin, Eprinomectin, Ivermectin, Selamectin, Moxidectin, pyrethrins, Nicotine, Matrine, Azadirachtin, rotenone, Tebufenpyrad, Pyridaben, Fenpyroximate, clofentezine, Propargite, Hexythiazox, Spirodiclofen, Fluacrypyrim, Ovex, or Pyridaben. The isothiazole oxime ether-containing strobilurin derivatives IV is present in the acaricidal composition in an amount between 1%-90% by mass percentage. The mass ratio of the isothiazole oxime ether-containing strobilurin derivatives IV to the above-described acaricidal agents is from 1%:99% to 99%:1%. The formulation processed by the acaricidal composition is chosen from suspension concentrates for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent. The insects controlled by the acaricidal composition are chosen from the genus *Aphididae*, the genus *Diptera*, the *eucalyptus*, the genus *Eucalyptus*, and the mites, world agricultural pests, forest pests, horticultural pests and health hazards. The plants controlled the acaricidal composition are chosen from rice, wheat, barley, oats, corn, sorghum, sweet potato, potato, tapioca, soybean, pea, broad bean, mung bean, adzuki bean, cotton, sericulture, peanuts, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, rape, onion, garlic, watermelon, melon, cantaloupe, apple, citrus and peach, tea, wild vegetables, bamboo shoots, hops, banana, papaya, orchid, or bonsai.

TABLE 1

Structure and physical and chemical parameters of the isothiazole oxime ether-containing strobilurin derivatives IV of the present invention

| Number | Name | Structure | m.p./° C. | $^1$HNMR(CDCl$_3$, 400 MHz, ppm) | Yield % | Shape |
|---|---|---|---|---|---|---|
| 1 | CL03-49 | (structure) | 100-102 | δ7.53(s, 1H, C=CH), 7.42-7.36(m, 1H, Ph—H), 7.31-7.23(m, 2H, Ph—H), 7.13-7.07(m, 1H, Ph—H), 5.20 (s, 2H, Ph—CH$_2$), 3.72(s, O—CH$_3$), 3.59(s, O—CH$_3$), 2.45(s, C—CH$_3$) | 59.14% | Yellow crystal |
| 2 | CL03-50 | (structure) | 61-63 | δ8.10(s, 1H, O=C—H), 7.54 (s, 1H C=CH), 7.39 (dd, J = 5.4, 3.6 Hz, Ph—H), 7.28(dd, J = 5.7, 3.4 Hz, 2H, Ph—H), 7.11(dd, J = 5.4, 3.5 Hz, 1H, Ph—H), 5.08(s, 2H, Ph—CH$_2$), 3.77 (s, 3H, O—CH$_3$), 3.63(s, 3H, O—CH$_3$) | 56.82% | Yellow crystal |
| 3 | CL04-03 | (structure) | 105-107 | δ7.61(s, 1H, C=CH—O), 7.48(dd, J = 8.3, 4.9 Hz, 1H, Ph—H), 7.37(dd, J = 5.3, 3.8 Hz, 2H, Ph—H), 7.22-7.18(m, 1H, Ph—H), 5.29(s, 2H, NH$_2$), 5.02(s, 2H, Ph—CH$_2$), 3.84(s, 3H, O—CH$_3$), 3.73(s, 3H, O—CH$_3$) | 97.83% | Yellow solid |
| 4 | CL04-04-A | (structure) | 36-38 | δ7.51(s, 1H, C=CH—O), 7.33(dd, J = 5.9, 3.1 Hz, 1H, Ph—H), 7.29-7.24 (m, 2H, Ph—H), 7.12-7.06(m, 1H, Ph—H), 5.22(ddd, J = 9.0, 3.7, 2.7 Hz, O—CH), 4.94 (s, 1H, Ph—CH$_2$) 3.78-3.73(s, 3H, O—CH$_3$), 3.62(s, 3H, O—CH$_3$), 2.73(dd, J = 16.9, 2.4 Hz, 1H, N=C—CH$_2$), 2.42(dd, J = 16.8, 9.1 Hz, 1H, N=C—CH$_2$), 1.81(s, 3H, N=C—CH$_3$) | 92.11% | Light Yellow solid |

TABLE 1-continued

Structure and physical and chemical parameters of the isothiazole oxime ether-containing strobilurin derivatives IV of the present invention

| Number | Name | Structure | m.p./° C. | ¹HNMR(CDCl₃, 400 MHz, ppm) | Yield % | Shape |
|---|---|---|---|---|---|---|
| 5 | CL04-04-B | 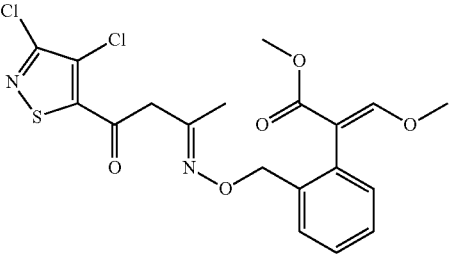 [SMILES: CO/C=C(/C(=O)OC)c1ccccc1CO/N=C(\C)CC(=O)c1snc(Cl)c1Cl] | 103-105 | δ11.74(s, 1H, O=C—CH₂), 7.53(s, 1H, C=CH—O), 7.36(m, 1H, Ph—H), 7.33 7.23(m, 2H, Ph—H), 7.11 (m, 2H, Ph—H), 5.92(s, 1H, O=C—CH₂), 4.98 (s, 2H, Ph—CH₂), 3.77 (s, 3H, O—CH₃), 3.63 (s, 3H, O—CH₃), 2.00 (s, 3H, N=C—CH₃) | 47.62% | Yellow solid |
| 6 | CL04-06 | 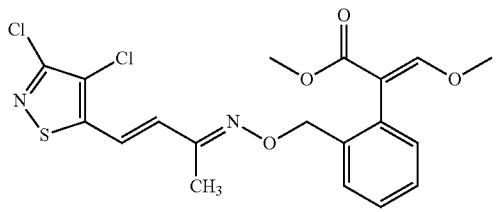 [SMILES: CO/C=C(/C(=O)OC)c1ccccc1CO/N=C(C)/C=C/c1snc(Cl)c1Cl] | 101-103 | δ7.57(s, 1H, C=CH—O), 7.45(dd, J = 7.3, 4.5 Hz, 2H, CH=CH, Ph—H), 7.35-7.31(m, 2H, Ph—H), 7.19-7.15(m, 1H, Ph—H), 6.88(d, J = 16.7 Hz, 1H, CH=CH), 5.09(s, 2H, Ph—CH₂), 3.81(s, 3H, O—CH₃), 3.67(s, 3H, O—CH₃), 2.11(s, 3H, N=C—CH₃) | 40.00% | White solid |
| 7 | CL04-15A | 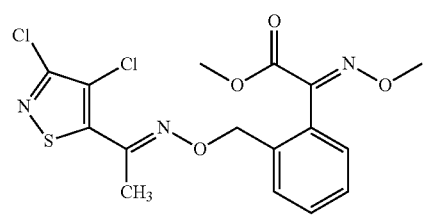 [SMILES: CO/N=C(/C(=O)OC)c1ccccc1CO/N=C(\C)c1snc(Cl)c1Cl] | 73-75 | δ7.51(s, 1H, Ph—H), 7.47-7.43(m, 2H, Ph—H), 7.24-7.20 (m, 1H, Ph—H), 5.23 (s, 2H, Ph—CH₂), 4.06 (s, 3H, O—CH₃), 3.83 (s, 3H, O—CH₃), 2.52 (s, 3H, N=C—CH₃) | 71.43% | Light yellow power |
| 8 | CL04-15B | 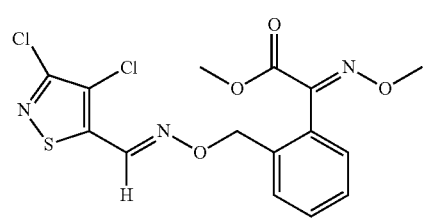 [SMILES: CO/N=C(/C(=O)OC)c1ccccc1CO/N=C/c1snc(Cl)c1Cl] | 88-90 | δ7.74(s, 1H, N=C—H), 7.42(s, 1H, Ph—H), 7.37(dd, J = 6.9, 2.9 Hz, 2H, Ph—H), 7.15-7.12 (m, 1H, Ph—H), 5.22(s, 2H, Ph—CH₂), 3.96(s, 3H, O—CH₃), 3.72(s, 3H, O—CH₃) | 72.73% | Light yellow power |
| 9 | CL04-15C | 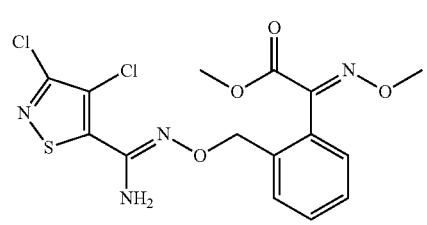 | 104-106 | δ7.40-7.30(m, 3H, Ph—H), 7.13(d, J = 6.4 Hz, 1H, Ph—H), 5.18(s, 2H, NH₂), 4.91 (s, 2H, Ph—CH₂), 3.97 (s, 3H, O—CH₃), 3.79 (s, 3H, O—CH₃) | 42.96% | Brownish yellow crystal |
| 10 | CL04-22A | 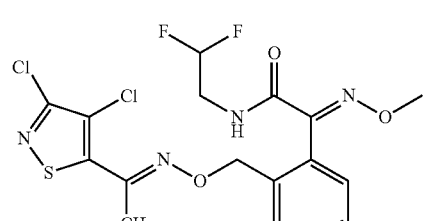 | 78-80 | δ7.57-7.39(m, 3H, Ph—H), 7.22(dd, J = 6.7, 1.9 Hz, 1H, Ph—H), 7.11(s, 1H, Ph—H), 5.91(tdd, J = 55.9, 8.6, 4.3 Hz, 1H, CHF₂), 5.18(d, J = 38.8 Hz, 2H, Ph—CH₂), 4.00(d, J = 13.8 Hz, 3H, O—CH₃), 3.83-3.65(m, 2H, N—CH₂), 2.42(d, J = 72.2 Hz, 3H, N=C—CH₃) | 95.00% | White crystal |

TABLE 1-continued

Structure and physical and chemical parameters of the isothiazole oxime ether-containing strobilurin derivatives IV of the present invention

| Number | Name | Structure | m.p./° C. | $^1$HNMR(CDCl$_3$, 400 MHz, ppm) | Yield % | Shape |
|---|---|---|---|---|---|---|
| 11 | CL04-22B | 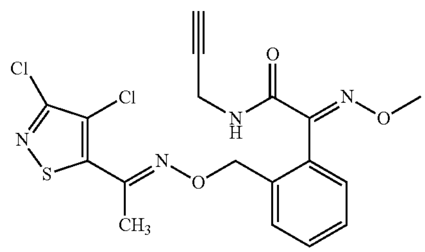 [SMILES: C#CCNC(=O)/C(=N/OC)c1ccccc1CO/N=C(\C)c1snc(Cl)c1Cl] | 120-122 | δ7.50(s, 1H, Ph—H), 7.44(dd, J = 9.6, 5.3 Hz, 2H, Ph—H), 7.22 (d, J = 6.8 Hz, 1H, Ph—H), 6.99(s, 1H, O=C—NH), 5.24(s, 2H, Ph—CH$_2$), 4.14(d, J = 5.2 Hz, 2H, N—CH$_2$), 3.98(s, 3H, O—CH$_3$), 2.42(d, J = 70.7 Hz, 3H, N=C—CH$_3$), 2.29(d, J = 9.0 Hz, 1H, C≡CH) | 95% | White crystal |
| 12 | CL04-22C | 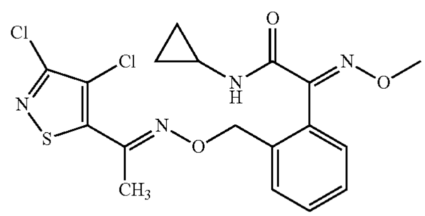 [SMILES: CO/N=C(/C(=O)NC1CC1)c1ccccc1CO/N=C(\C)c1snc(Cl)c1Cl] | 115-117 | δ7.50(d, J = 7.0 Hz, 1H, Ph—H), 7.42 (dt, J = 11.5, 8.0 Hz, 2H, Ph—H), 7.22(d, J = 6.7 Hz, 1H, Ph—H), 6.87(s, 1H, O=C—NH), 5.24(s, 2H,, Ph—CH$_2$), 3.93(s, 3H, O—CH$_3$), 2.78 (d, J = 3.6 Hz, 1H, N—CH), 2.51(s, 3H, N=C—CH$_3$), 0.82(d, J = 6.3 Hz, 2H, cyclopropyl-CH$_2$), 0.59 (s, 2H, cyclopropyl-CH$_2$) | 72.73% | Colorless crystal |
| 13 | CL04-22D | 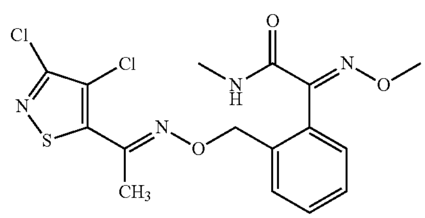 | 79-81 | δ7.52-7.44(m, 1H, Ph—H), 7.40(dd, J = 9.4, 5.8 Hz, 2H, Ph—H), 7.21(d, J = 7.2 Hz, 1H, Ph—H), 6.92(d, J = 4.5 Hz, 1H, O=C—NH), 5.25(s, 2H, Ph—CH$_2$), 3.91(s, 3H, O—CH$_3$), 2.84(d, J = 4.9 Hz, 3H, N—CH$_3$), 2.48(s, 3H, N=C—CH$_3$) | 70.97% | White solid |
| 14 | CL04-22E | 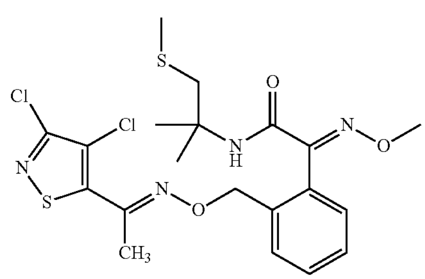 [SMILES: CO/N=C(/C(=O)NC(C)(C)CSC)c1ccccc1CO/N=C(\C)c1snc(Cl)c1Cl] | — | δ7.47(d, J = 6.8 Hz, 1H, Ph—H), 7.44-7.38 (m, 2H, Ph—H), 7.23-7.19(m, 1H, Ph—H), 6.93(s, 1H, O=C—NH), 5.15(s, 2H, Ph—CH$_2$), 3.99(s, 3H, O—CH$_3$), 3.00(s, 2H, S—CH$_2$), 2.37(s, 3H, N=C—CH$_3$), 2.19(s, 3H, S—CH$_3$), 1.49 (s, 6H, CH$_3$—C—CH$_3$) | 36.84% | Yellow oil |
| 15 | CL04-22F | 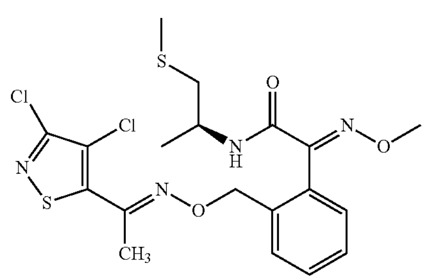 | 35-37 | δ7.44(dd, J = 7.2, 4.1 Hz, 1H, Ph—H), 7.42-7.37(m, 2H, Ph—H), 7.20(d, J = 6.7 Hz, 1H, Ph—H), 6.88(d, J = 8.0 Hz, 1H, O=C—NH), 5.13(s, 2H, Ph—CH$_2$), 4.24(dt, J = 13.4, 6.6 Hz, 1H, N—CH), 3.98 (s, 3H, O—CH$_3$), 2.72 (dd, J = 13.5, 5.5 Hz, 1H, S—CH$_2$), 2.63(dd, J = 13.5, 6.4 Hz, 1H, S—CH$_2$), 2.33(s, 3H, N=C—CH$_3$), 2.15(s, 3H, S—CH$_3$), 1.32(d, J = 6.6 Hz, 3H, N—C—CH$_3$) | 37.84% | White power |

TABLE 1-continued

Structure and physical and chemical parameters of the isothiazole oxime ether-containing strobilurin derivatives IV of the present invention

| Number | Name | Structure | m.p./° C. | ¹HNMR(CDCl₃, 400 MHz, ppm) | Yield % | Shape |
|---|---|---|---|---|---|---|
| 16 | CL04-24 | 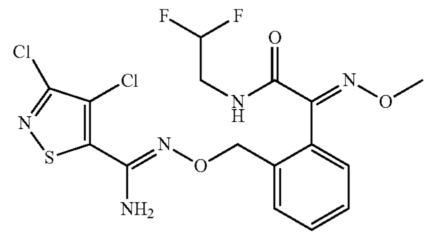 [SMILES: CO/N=C(/C(=O)NCC(F)F)c1ccccc1CO/N=C(\N)c1snc(Cl)c1Cl] | 118-120 | δ7.37(s, 1H, Ph—H), 7.35-7.30(m, 2H, Ph—H), 7.13-7.08(m, 1H, Ph—H), 7.02(s, 1H, O=C—NH), 5.84 (tt, J = 55.9, 4.0 Hz, 1H, CHF₂), 5.18(s, 2H, NH₂), 4.88(s, 2H, Ph—CH₂), 3.92(s, 3H, O—CH₃), 3.73-3.60(m, 2H, N—CH₂) | 76.60% | Colorless crystal |
| 17 | CL04-25A | 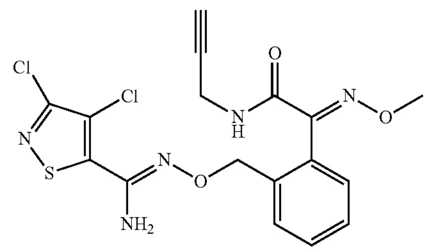 | 106-108 | δ7.36(t, J = 3.6 Hz, 1H, Ph—H), 7.35-7.31(m, 2H, Ph—H), 7.10(dd, J = 5.8, 3.0 Hz, 1H, Ph—H), 6.92(s, 1H, O=C—NH), 5.21(s, 2H, NH₂), 4.88(s, 2H, Ph—CH₂), 4.08 (dd, J = 5.4, 2.5 Hz, 2H, N—CH₃), 3.91(s, 3H, O—CH₃), 2.17(t, J = 2.5 Hz, 1H, C≡CH) | 71.43% | White solid |
| 18 | CL04-25B | 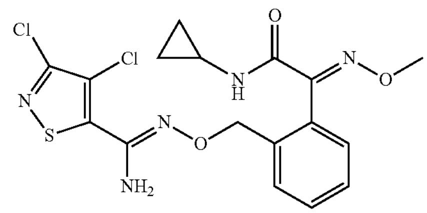 [SMILES: CO/N=C(/C(=O)NC1CC1)c1ccccc1CO/N=C(\N)c1snc(Cl)c1Cl] | 12-128 | δ7.38-7.35(m, 1H, Ph—H), 7.34-7.30(m, 2H, Ph—H), 7.11-7.08 (m, 1H, Ph—H), 6.80 (s, 1H, O=C—NH), 5.27(s, 2H, NH₂), 4.87 (s, 2H, Ph—CH₂), 3.87 (s, 3H, O—CH₃), 2.77-2.70(m, 1H, N—CH), 0.73 (dd, J = 7.0, 5.4 Hz, 2H, cyclopropyl-CH₂), 0.55-0.50(m, 2H, cyclopropyl-CH₂) | 48.71% | White power |
| 19 | CL04-25C | 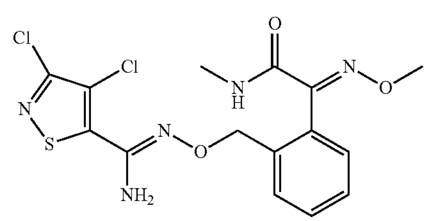 [SMILES: CNC(=O)/C(=N/OC)c1ccccc1CO/N=C(\N)c1snc(Cl)c1Cl] | 122-124 | δ7.37(d, J = 5.7 Hz, 1H, Ph—H), 7.32(dd, J = 6.0, 3.1 Hz, 2H, Ph—H), 7.12-7.08(m, 1H, Ph—H), 6.73(d, J = 3.8 Hz, 1H, O=C—NH), 5.25(s, 2H, NH₂), 4.88(s, 2H, Ph—CH₂), 3.88(s, 3H, O—CH₃), 2.84(d, J = 5.0 Hz, 3H, N—CH₃) | 39.39% | White power |
| 20 | CL04-25D | 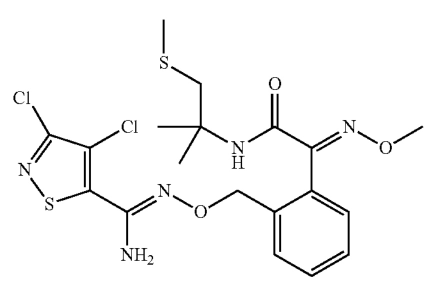 [SMILES: CO/N=C(/C(=O)NC(C)(C)CSC)c1ccccc1CO/N=C(\N)c1snc(Cl)c1Cl] | 28-30 | δ7.44(dd, J = 5.9, 3.3 Hz, 1H, Ph—H), 7.40-7.36(m, 2H, Ph—H), 7.16(dd, J = 5.6, 3.3 Hz, 1H, Ph—H), 6.91 (s, 1H, O=C—NH), 5.35(s, 2H, NH₂), 4.96 (s, 2H, Ph—CH₂), 3.96 (s, 3H, O—CH₃), 2.98 (s, 2H, S—CH₂), 2.16 (s, 3H, S—CH₃), 1.46 (s, 6H, CH₃—C—CH₃) | 58.06% | Yellow-transparent crystal |

TABLE 1-continued

Structure and physical and chemical parameters of the isothiazole oxime ether-containing strobilurin derivatives IV of the present invention

| Number | Name | Structure | m.p./° C. | $^1$HNMR(CDCl$_3$, 400 MHz, ppm) | Yield % | Shape |
|---|---|---|---|---|---|---|
| 21 | CL04-25E | 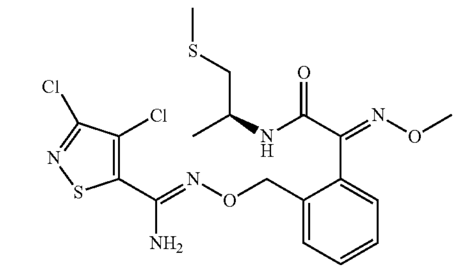 | — | δ7.44(dd, J = 3.9, 1.9 Hz, 1H, Ph—H), 7.41-7.38(m, 2H, Ph—H), 7.20-7.16(m, 1H, Ph—H), 6.91(d, J = 8.2 Hz, 1H, O=C—NH), 5.34(s, 2H, NH$_2$), 4.96(s, 2H, Ph—CH$_2$), 4.29-4.21(m, 1H, N—CH), 3.97(s, 3H, O—CH$_3$), 2.73(dd, J = 13.5, 5.5 Hz, 1H, S—CH$_2$), 2.64(dd, J = 13.5, 6.4 Hz, 1H, S—CH$_2$), 2.15(s, 3H, S—CH$_3$), 1.32(d, J = 6.6 Hz, 3H, N—CH—CH$_3$) | 44.19% | Yellow oil |
| 22 | CL04-17 | 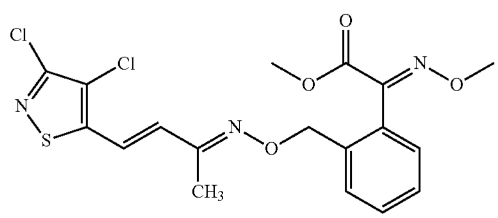 [SMILES: CO/N=C(/C(=O)OC)c1ccccc1CO/N=C(C)/C=C/c1snc(Cl)c1Cl] | 105-107 | δ7.35(ddd, J = 9.6, 6.1, 2.0 Hz, 3H, Ph—H), 7.14-7.11 (m, 1H, Ph—H), 6.75 (d, J = 5.1 Hz, 2H, CH=CH), 5.02(s, 2H, Ph—CH$_2$), 3.97(s, 3H, O—CH$_3$), 3.79(s, 3H, N—CH$_3$), 1.97(s, 3H, C=C—CH$_3$) | 60.00% | white power |
| 23 | CL04-32A | 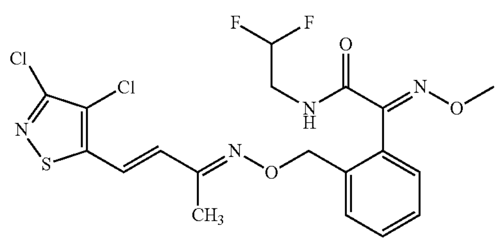 [SMILES: CO/N=C(/C(=O)NCC(F)F)c1ccccc1CO/N=C(C)/C=C/c1snc(Cl)c1Cl] | 98-100 | δ7.47-7.36(m, 4H, CH=CH, Ph—H), 7.21-7.16(m, 1H, Ph—H), 7.07(d, J = 5.8 Hz, 1H, O=C—NH), 6.87 (d, J = 16.7 Hz, 1H, CH=CH), 5.86(tt, J = 55.9, 4.1 Hz, 1H, CHF$_2$), 5.05(s, 2H, Ph—CH$_2$), 3.97(s, 3H, O—CH$_3$), 3.80-3.63(m, 2H, N—CH$_2$), 2.09(s, 3H, N=C—CH$_3$) | 53.57% | White solid |
| 24 | CL04-32B | 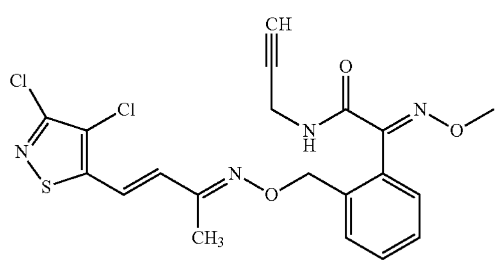 [SMILES: C#CCNC(=O)/C(=N/OC)c1ccccc1CO/N=C(C)/C=C/c1snc(Cl)c1Cl] | 92-93 | δ7.47-7.35(m, 4H, CH=CH, Ph—H), 7.21-7.17(m, 1H, Ph—H), 7.00-6.91(m, 1H, O=C—NH), 6.82(d, J = 3.7 Hz, 1H, CH=CH), 5.05(s, 2H, Ph—CH$_2$), 4.17(s, 1H, N—CH$_2$), 4.12-4.09(m, 1H, N—CH$_2$), 3.97(s, 3H, O—CH$_3$), 2.26(dt, J = 6.8, 2.6 Hz, 1H, C≡CH), 2.05(s, 3H, N=C—CH$_3$) | 62.96% | White solid |
| 25 | CL04-32C | 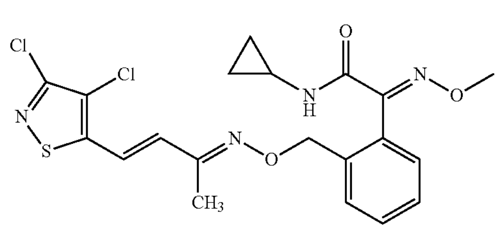 [SMILES: CO/N=C(/C(=O)NC1CC1)c1ccccc1CO/N=C(C)/C=C/c1snc(Cl)c1Cl] | 95-97 | δ7.50-7.36(m, 4H, CH=CH, Ph—H), 7.22 (d, J = 6.9 Hz, 1H, Ph—H), 6.86(t, J = 6.0 Hz, 2H, O=C—NH, CH=CH), 5.11(s, 2H, Ph—CH$_2$), 3.97(s, 3H, O—CH$_3$), 2.07(s, 3H, N=C—CH$_3$), 0.84(d, J = 5.6 Hz, 2H, cyclopropyl-CH$_2$), 0.62 (dd, J = 3.7, 1.7 Hz, 2H, cyclopropyl-CH$_2$) | 59.26% | White power |

TABLE 1-continued

Structure and physical and chemical parameters of the isothiazole oxime ether-containing strobilurin derivatives IV of the present invention

| Number | Name | Structure | m.p./° C. | ¹HNMR(CDCl₃, 400 MHz, ppm) | Yield % | Shape |
|---|---|---|---|---|---|---|
| 26 | CL04-32D | 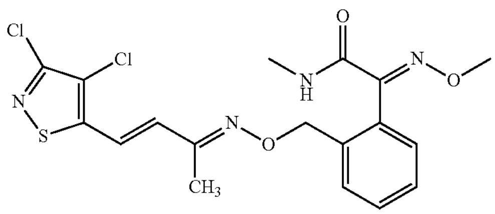 [SMILES: CNC(=O)/C(=N/OC)c1ccccc1CO/N=C(C)/C=C/c1snc(Cl)c1Cl] | 137-139 | δ7.48-7.35(m, 4H, CH=CH, Ph—H), 7.21-7.16(m, 1H, Ph—H), 6.81(d, J = 3.7 Hz, 1H, CH=CH), 6.77(s, 1H, O=C—NH), 5.09(s, 2H, Ph—CH₂), 3.96(s, 3H, O—CH₃), 2.93(d, J = 5.0 Hz, 3H, N—CH₃), 2.04(s, 3H, N=C—CH₃) | 65.38% | transparent crystal |
| 27 | CL04-32E | 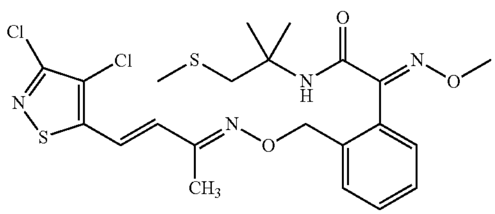 [SMILES: CO/N=C(/C(=O)NC(C)(C)CSC)c1ccccc1CO/N=C(C)/C=C/c1snc(Cl)c1Cl] | — | δ7.47-7.34(m, 4H, CH=CH, Ph—H), 7.18 (d, J = 7.3 Hz, 1H, Ph—H), 6.89(d, J = 2.9 Hz, 1H, O=C—NH), 6.83(s, 1H, CH=CH), 5.09(d, J = 17.2 Hz, 2H, Ph—CH₂), 3.97(s, 3H, O—CH₃), 2.98(s, 2H, S—CH₂), 2.16(s, 3H, S—CH₃), 2.07(s, 3H, N=C—CH₃), 1.47(s, 6H, CH₃—C—CH₃) | 100% | Yellow oil |
| 28 | CL04-32F | 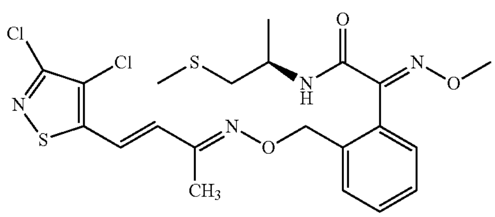 [SMILES: CO/N=C(/C(=O)N[C@H](C)CSC)c1ccccc1CO/N=C(C)/C=C/c1snc(Cl)c1Cl] | — | δ7.41-7.26(m, 4H, CH=CH, Ph—H), 7.12 (dd, J = 6.7, 2.0 Hz, 1H, Ph—H), 6.81(d, J = 4.5 Hz, 1H, O=CH—NH), 6.74(s, 1H, CH=CH), 5.03(s, 2H, Ph—CH₂), 4.16(dd, J = 13.3, 6.6 Hz, 1H, N—CH), 3.89(s, 3H, O—CH₃), 2.68-2.47(m, 2H, S—CH₂), 2.07(s, 3H, S—CH₃), 1.98(s, 3H, N=C—CH₃), 1.24 (d, J = 6.7 Hz, 3H, N—C—CH₃) | 84.62% | Yellow oil |
| 29 | CL04-00 | 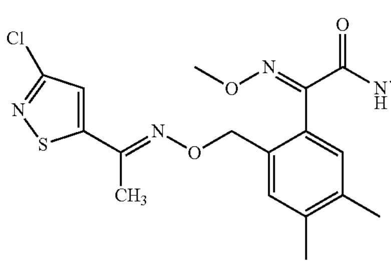 | — | — | 68.22% | — |
| 30 | CL04-00 | 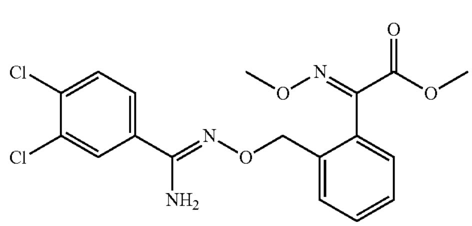 [SMILES: CO/N=C(/C(=O)OC)c1ccccc1CO/N=C(\N)c1ccc(Cl)c(Cl)c1] | 111-113 | δ7.70 (s, 1H, Ph—H), 7.51-7.36 (m, 5H, Ph—H), 7.20 (d, J = 7.2 Hz, 1H, Ph—H), 5.01 (s, 2H, Ph—CH₂), 4.74 (s, 2H, —NH₂), 4.04 (s, 3H, O—CH₃), 3.84 (s, 3H, N—CH₃). | 55.57% | White crystal |

TABLE 2

Fungicidal activity of the isothiazole oxime ether-containing strobilurin derivatives IV of the present invention (50 μg/mL, inhibition/%)

| Number | Name | AS | CA | GZ | PP | BC | SS | RC | PS | PI |
|---|---|---|---|---|---|---|---|---|---|---|
| 1 | CL03-49 | 42.86 | 66.67 | 52.17 | 78.26 | 100 | 80.00 | 100 | 64.71 | 52.63 |
| 2 | CL03-50 | 57.14 | 66.67 | 73.91 | 78.26 | 100 | 53.33 | 100 | 64.71 | 57.89 |
| 3 | CL04-03 | 57.14 | 100 | 60.87 | 86.96 | 100 | 100 | 100 | 58.82 | 47.37 |
| 4 | CL04-04-A | 85.71 | 75.00 | 60.87 | 73.91 | 100 | 90.00 | 100 | 52.94 | 42.11 |
| 5 | CL04-04-B | 50.00 | 75.00 | 73.91 | 60.87 | 58.33 | 76.67 | 92.59 | 64.71 | 52.63 |
| 6 | CL04-06 | 57.14 | 50.00 | 73.91 | 73.91 | 100 | 100 | 100 | 70.59 | 78.95 |
| 7 | CL04-15A | 47.06 | 50.00 | 41.18 | 53.03 | 100 | 100 | 85.45 | 76.92 | 78.95 |
| 8 | CL04-15B | 100 | 91.67 | 70.59 | 62.12 | 100 | 90.00 | 98.18 | 69.23 | 94.74 |
| 9 | CL04-15C | 52.94 | 75.00 | 94.44 | 71.21 | 100 | 98.00 | 89.09 | 76.92 | 89.47 |
| 10 | CL04-22A | 37.14 | 42.86 | 78.95 | 40.35 | 53.85 | 84.00 | 87.70 | 20.00 | 80.00 |
| 11 | CL04-22B | 28.57 | 35.71 | 100 | 49.12 | 51.92 | 100 | 86.89 | 73.33 | 80.00 |
| 12 | CL04-22C | 27.87 | 44.00 | 63.64 | 61.40 | 47.37 | 80.00 | 60.98 | 56.76 | 100 |
| 13 | CL04-22D | 47.54 | 87.50 | 100 | 80.77 | 100 | 100 | 100 | 89.19 | 100 |
| 14 | CL04-22E | 27.27 | 45.83 | 51.52 | 42.86 | 62.50 | 29.41 | 76.00 | 21.21 | 28.57 |
| 15 | CL04-22F | 16.36 | 12.50 | 33.33 | 32.77 | 45.54 | 52.94 | 76.00 | 15.15 | 17.14 |
| 16 | CL04-24 | 12.73 | 16.67 | 33.33 | 39.50 | 37.50 | 52.94 | 62.00 | 24.24 | 22.86 |
| 17 | CL04-25A | 8.20 | 20.00 | 54.55 | 19.30 | 42.11 | 46.67 | 65.85 | 45.95 | 100 |
| 18 | CL04-25B | 21.31 | 28.00 | 63.64 | 22.81 | 36.84 | 73.33 | 85.37 | 18.92 | 33.33 |
| 19 | CL04-25C | 34.43 | 44.00 | 100 | 40.35 | 57.89 | 66.67 | 100 | 83.78 | 100 |
| 20 | CL04-25D | 16.36 | 12.50 | 21.21 | 27.73 | 39.29 | 52.94 | 62.00 | 15.15 | 17.14 |
| 21 | CL04-25E | 9.09 | 16.67 | 45.45 | 10.92 | 35.71 | 52.94 | 54.00 | 21.21 | 11.43 |
| 22 | CL04-17 | 35.71 | 50.00 | 60.87 | 47.83 | 100 | 86.67 | 81.48 | 58.82 | 47.37 |
| 23 | CL04-32A | 34.43 | 36.00 | 45.45 | 29.82 | 52.63 | 53.33 | 85.37 | 35.14 | 90.48 |
| 24 | CL04-32B | 40.98 | 52.00 | 81.82 | 64.91 | 47.37 | 80.00 | 100 | 78.38 | 100 |
| 25 | CL04-32C | 47.54 | 60.00 | 63.64 | 71.93 | 57.89 | 73.33 | 70.73 | 67.57 | 100 |
| 26 | CL04-32D | 54.10 | 84.00 | 100 | 64.91 | 84.21 | 73.33 | 85.37 | 89.19 | 100 |
| 27 | CL04-32E | 5.45 | 12.50 | 24.24 | 39.50 | 32.14 | 41.18 | 58.00 | 15.15 | 11.43 |
| 28 | CL04-32F | 12.73 | 12.50 | 60.61 | 57.98 | 42.86 | 52.94 | 62.00 | 21.21 | 20.00 |
| 29 | CL04-00 | 21.54 | 22.60 | 29.63 | 36.97 | 32.44 | 22.64 | 12.03 | 21.28 | 32.02 |
| 30 | CL04-00 | 44.44 | 65.00 | 50.00 | 61.21 | 75.00 | 66.67 | 85.71 | 53.91 | 76.36 |
| 31 | Azoxystrobin | 75.00 | 55.56 | 71.43 | 100 | 91.18 | 88.10 | 84.06 | 80.77 | 46.88 |
| 32 | Enestroburin | 50.00 | 55.22 | 21.54 | 59.09 | 48.57 | 44.00 | 73.97 | 57.50 | 32.97 |

TABLE 3

Fungicidal Efficacy of the isothiazole oxime ether-containing strobilurin derivatives IV of the present invention against *S. fuliginea*

| Compd. | rate (g/hm²) | Base DI[b] | After DI[c] | field efficacy (%) | DD[a] 5% | 1% |
|---|---|---|---|---|---|---|
| 9.60% CL04-22D EC | 37.5 | 1.98 | 8.01 | 78.62 | a | A |
| 250 g/L Azoxystrobin SC | 37.5 | 1.66 | 9.59 | 70.19 | b | B |
| 50% Trifloxystrobin WG | 37.5 | 1.64 | 10.04 | 68.02 | b | B |
| CK | — | 1.07 | 20.63 | — | — | — |

[a]DD, distinct difference.
[b]Base DI, disease index base.
[c]After DI, disease index after compound application.

TABLE 4

Fungicidal Efficacy of the isothiazole oxime ether-containing strobilurin derivatives IV of the present invention against *P. cubensis*

| Compd. | rate (g/hm²) | Base DI[b] | After DI[c] | Field efficacy (%) | DD[a] 5% |
|---|---|---|---|---|---|
| 9.60% CL04-22D EC | 75 | 3.71 | 5.39 | 79.18 | a |
| 50% Trifloxystrobin WG | 75 | 3.73 | 7.24 | 72.02 | b |
| 250 g/L Pyraclostrobin EC | 75 | 3.57 | 5.78 | 77.52 | a |
| CK | — | 3.58 | 24.96 | — | — |

[a]DD, distinct difference.
[b]Base DI, disease index base.
[c]After DI, disease index after compound application.

TABLE 5

Anti-TMV activity of the isothiazole oxime ether-containing strobilurin derivatives IV of the present invention (100 μg/mL, inhibition/%)

| Number | Name | Curative effect | Inactivation effect | Protection effect | Induction effect |
|---|---|---|---|---|---|
| 1 | CL03-49 | 39.41 ± 2.99 | 52.48 ± 0.64 | 35.90 ± 0.63 | 75.90 ± 0.83 |
| 2 | CL03-50 | 48.32 ± 5.88 | 70.19 ± 0.41 | 54.02 ± 0.51 | 84.02 ± 5.51 |
| 3 | CL04-03 | 45.04 ± 4.15 | 81.75 ± 2.83 | 35.13 ± 0.39 | 75.13 ± 0.69 |
| 4 | CL04-04-A | 19.10 ± 2.13 | 75.46 ± 7.91 | 61.60 ± 1.25 | 71.60 ± 1.55 |
| 5 | CL04-04-B | 19.10 ± 2.00 | 65.46 ± 7.46 | 45.46 ± 3.70 | 55.46 ± 6.70 |

TABLE 5-continued

Anti-TMV activity of the isothiazole oxime ether-containing
strobilurin derivatives IV of the present invention (100 μg/mL, inhibition/%)

| Number | Name | Curative effect | Inactivation effect | Protection effect | Induction effect |
|---|---|---|---|---|---|
| 6 | CL04-06 | 22.43 ± 6.85 | 22.22 ± 5.90 | 54.08 ± 3.81 | 74.08 ± 5.81 |
| 7 | CL04-15A | 1.52 ± 0.62 | 54.76 ± 1.26 | 40.53 ± 0.84 | 70.53 ± 0.84 |
| 8 | CL04-15B | 27.00 ± 4.13 | 52.13 ± 6.48 | 14.74 ± 2.73 | 74.74 ± 2.73 |
| 9 | CL04-15C | 1.52 ± 0.62 | 59.94 ± 2.76 | 25.08 ± 4.33 | 85.08 ± 5.33 |
| 10 | CL04-22A | 23.44 ± 5.58 | 49.90 ± 3.63 | 30.71 ± 2.06 | 60.71 ± 2.26 |
| 11 | CL04-22B | 1.52 ± 0.62 | 36.70 ± 4.98 | 53.10 ± 0.75 | 53.10 ± 0.75 |
| 12 | CL04-22C | 4.62 ± 0.55 | 4.44 ± 0.85 | 23.57 ± 0.57 | 83.57 ± 0.07 |
| 13 | CL04-22D | 32.78 ± 3.36 | 4.44 ± 0.85 | 49.05 ± 2.77 | 79.05 ± 7.77 |
| 14 | CL04-22E | 20.25 ± 5.58 | 45.40 ± 2.20 | 22.71 ± 2.05 | 12.71 ± 6.05 |
| 15 | CL04-22F | 1.52 ± 0.62 | 0 | 23.76 ± 3.42 | 63.76 ± 3.52 |
| 16 | CL04-24 | 14.96 ± 3.08 | 27.30 ± 6.56 | 36.78 ± 5.50 | 46.78 ± 7.70 |
| 17 | CL04-25A | 82.36 ± 5.02 | 0 | 40.74 ± 2.51 | 70.74 ± 2.81 |
| 18 | CL04-25B | 20.51 ± 1.84 | 0 | 19.56 ± 3.36 | 18.56 ± 3.76 |
| 19 | CL04-25C | 14.68 ± 4.84 | 0 | 59.82 ± 4.23 | 69.82 ± 5.27 |
| 20 | CL04-25D | 35.93 ± 1.63 | 0 | 21.15 ± 1.69 | 21.15 ± 3.69 |
| 21 | CL04-25E | 19.12 ± 6.56 | 0 | 26.00 ± 4.71 | 16.00 ± 7.71 |
| 22 | CL04-17 | 31.56 ± 3.95 | 35.93 ± 1.53 | 29.27 ± 1.31 | 39.27 ± 1.41 |
| 23 | CL04-32A | 1.52 ± 0.62 | 37.75 ± 6.62 | 45.32 ± 2.00 | 45.32 ± 2.00 |
| 24 | CL04-32B | 81.33 ± 5.49 | 72.13 ± 5.59 | 23.43 ± 1.02 | 73.43 ± 4.09 |
| 25 | CL04-32C | 31.56 ± 3.91 | 41.40 ± 0.92 | 19.00 ± 0.72 | 16.00 ± 7.71 |
| 26 | CL04-32D | 1.52 ± 0.62 | 69.27 ± 1.02 | 39.07 ± 2.73 | 39.07 ± 2.73 |
| 27 | CL04-32E | 1.52 ± 0.62 | 13.65 ± 0.55 | 40.79 ± 0.77 | 70.79 ± 3.77 |
| 28 | CL04-32F | 63.67 ± 5.66 | 7.71 ± 1.42 | 53.40 ± 4.73 | 63.40 ± 6.73 |
| 29 | CL04-00 | 27.32 ± 1.24 | 20.68 ± 2.10 | 26.30 ± 2.47 | 20.34 ± 2.16 |
| 30 | CL04-00 | 26.39 ± 1.22 | 19.68 ± 1.10 | 25.30 ± 1.47 | 19.34 ± 1.14 |
| 31 | Ningnanmycin | 74.10 ± 2.04 | — | — | — |
| 32 | TDL | — | — | — | 65.00 ± 2.00 |
| 33 | BTH | — | — | 78.10 ± 0.54 | 78.00 ± 1.34 |
| 34 | SZG-7 | — | — | — | 79.00 ± 2.27 |
| 35 | Ribavirin | — | 78.00 ± 1.00 | — | — |
| 36 | Isotianil | 27.31 ± 2.12 | 20.77 ± 7.30 | 24.80 ± 5.85 | 44.44 ± 5.18 |

INDUSTRIAL APPLICABILITY

The invention provides a class of the isothiazole oxime ether-containing strobilurin derivatives, a preparation method and application. The compounds of the invention provided can regulate the biological activity of plant pests and plant pathogens in agriculture, horticulture, sanitary and forestry, and also can be used in agriculture, horticulture, forestry, insecticide, acaricidal, fungicidal, anti-plant virus, induced plant defense responses, with good economic value and application prospects.

What is claimed is:

1. An isothiazole oxime ether-containing strobilurin compound, wherein the compound is:

CL03-49

CL04-03

, or

CL04-22D

, or

2. A composition comprising
an isothiazole oxime ether-containing strobilurin compound, wherein the compound is:

[Structure CL03-49: isothiazole (3,4-dichloro) with C(CH₃)=N-O-CH₂-phenyl-C(=C(OCH₃))C(=O)OCH₃]

, or

[Structure CL04-03: isothiazole (3,4-dichloro) with C(NH₂)=N-O-CH₂-phenyl-C(=C(OCH₃))C(=O)OCH₃]

, or

[Structure CL04-22D: isothiazole (3,4-dichloro) with C(CH₃)=N-O-CH₂-phenyl-C(=N-O-CH₃)C(=O)NHCH₃]

or a combination thereof.

3. The composition of claim 2, wherein the composition is formulated as an insecticide composition, a fungicide composition, an antiviral composition, an acaricide composition, a tobacco mosaic virus agent composition, a pesticide composition, a plant elicitor composition, or a plant activator composition.

4. The composition of claim 2, wherein the isothiazole oxime ether-containing strobilurin compound is present in the composition in an amount between 1%-90% by mass percentage.

5. The composition of claim 2, further comprising:
one or more insecticides;
one or more fungicides;
one or more anti-plant virus agents; or
one or more acaricides.

6. The composition of claim 5, wherein a mass ratio of the isothiazole oxime ether-containing strobilurin compound to the one or more insecticides, the one or more fungicides, the one or more anti-plant virus agents, or the one or more acaricides is from 99%:1% to 1%:99%.

7. The composition of claim 2, wherein the composition is formulated as a suspension concentrate for seed treatment, water emulsion, microemulsion, suspoemulsion, capsule suspension, water-soluble granule, fine granule, soluble concentrate, poisonous valley, block bait, granular bait, flake bait, concentrated bait, slow release block, electrostatic spray formulation, oil-in-water emulsion, smoke can, smoke candle, smoke tube, smoke stick, smoke sheet, smoke pill, gas generator, ointment, hot spray formulation, cold spray formulation, aerosol, solid liquid mixing agent, liquid/liquid mixing agent, solid/solid mixing agent, lacquer, granule, tracking powder, oil suspension, oil dispersible powder, thickener, pouring agent, seed coating agent, smear agent, film forming oil agent, ultra-low volume liquid agent, or steam release agent.

8. A method of controlling a plant disease or a plant pest, the method comprising:
applying an isothiazole oxime ether-containing strobilurin compound to one or more plants or to one or more insects to control a plant disease or a plant pest, wherein the isothiazole oxime ether-containing strobilurin compound is:

[Structure CL03-49]

, or

[Structure CL04-03]

, or

[Structure CL04-22D]

or a combination thereof.

9. The method of claim 8, wherein applying an isothiazole oxime ether-containing strobilurin compound to one or more plants or to one or more insects comprises applying the isothiazole oxime ether-containing strobilurin compound to control agricultural, forestry, or horticultural plant pests.

10. The method of claim 8, wherein applying an isothiazole oxime ether-containing strobilurin compound to one or more plants or to one or more insects to control a plant disease or a plant pest comprises applying an insecticidal composition comprising the isothiazole oxime ether-containing strobilurin compound to the one or more plants to control the plant pest,
the one or more plants comprising rice, wheat, barley, oats, corn, sorghum, sweet potato, potato, tapioca, soybean, pea, broad bean, pea, mung bean, adzuki bean, cotton, sericulture, peanut, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, rape, Onions, garlic, watermelon, melon, cantaloupe, papaya, apple, citrus and peach, tea, wild vegetables, bamboo shoots, hops, pepper, banana, papaya, orchid, or bonsai, and
the plant pest comprising *Tetranychus cinnbarinus*, *Locusta migratoria* manilensis, cypress locust, rice blast, Japanese yellow ridge, single locust, oriental carp, rice locust, scorpion horse, greenhouse hummer, rice tube hummer, wheat tube hummer, greenhouse whitefly, whitefly, black-tailed leafhopper, big green leafhopper, cotton leafhopper, spotted wax hopper, brown plant hopper, white-backed plant hopper, gray plant hopper, sugarcane, squared cornucopia, cotton aphid, wheat Fork, wheat long tube, peach aphid, sorghum, radish, blown sorghum, mulberry scorpion, scorpion shield, pear round scorpion, white wax worm, red wax scorpion, Korean ball scorpion, *stephanitis nashi esaki et takeya*, Banana nets, fine-horned flower buds, tiny flower buds, needle-edge mites, rice spider mites, rice brown mites, rice black mites, rice green mites, green blind mites, ticks, black scorpions, large grass mites, licao, chinese grasshopper, moth, moth, yellow moth, brown moth, flat moth, wheat moth, cotton bollworm, sweet potato moth, diamondback moth, peach small heartworm, soybean heartworm, peach small carnivorous worm, apple leaf roller moth, brown leaf moth, yellow leaf moth, sorghum, pea pod, corn borer, stem borer, rapeseed meal, rice leaf roller, stripe, roller leafhopper, peach aphid, armyworm, *Spodoptera litura*, rice blast, cotton small bridge worm, beet armyworm, giant salamander, cotton bollworm, dingdian diamond, small tiger, earth tiger, yellow tiger, toxic moth, gypsy moth, sweet potato hawk moth, bean hawk moth, straight grain rice butterfly, cryptic valley butterfly, citrus phoenix butterfly, jade belt phoenix butterfly, cabbage butterfly, ramie red butterfly, ramie butterfly, bean phthalocyanine, venus carapace, wrinkle-skinned armor, wheat-spotted armor, ditch-gold needle, fine-necked Golden Needle, *G. striata*, Black-skinned scorpion, citrus small jiding, lampralimbatagebler, *Tenebrio molitor*, Black mealworm, *tribolium castaneum* herbst, *Tribolium confusum* jac. du val., patina, golden tortoise, dark golden tortoise, north China black scorpion golden tortoise, mulberry ox, star celestial, orange brown hornbill, peach red neck horn, big worm leaf worm, small cockroach Leaf worm, yellow squash, yellow scalloped beetle, mung bean elephant, pea elephant, broad bean elephant, corn elephant, rice elephant, Dolerus Chu, pear fruit sawfly, yellow belt wasp, armyworm white star wasp, Chrysalis suspense, *Campoletis chlorideae* Uchida, *Verruca verruca*, mosquito, fly, horsefly, wheat blossom midge, wheat midge, rice gall midge, *Tetradacus citri*, Melon fruit fly, wheat fly ash, Leafminer, soybean stem borer, wheat straw flies, seed fly, onion fly, carrot fly, *Exorista civilis* Rondani, Mailing flies of corn borer, or armyworm.

11. The method of claim 8, wherein applying an isothiazole oxime ether-containing strobilurin compound to one or more plants or to one or more insects to control a plant disease or a plant pest comprises applying a fungicidal composition comprising the isothiazole oxime ether-containing strobilurin compound to the one or more plants to control the plant disease,
the one or more plants comprising rice, wheat, barley, oats, corn, sorghum, sweet potato, potato, tapioca, soybean, pea, broad bean, pea, mung bean, adzuki bean, cotton, sericulture, peanut, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, rape, Onions, garlic, watermelon, melon, cantaloupe, papaya, apple, citrus and peach, tea, wild vegetables, bamboo shoots, hops, pepper, banana, papaya, orchid, or bonsai, and
the plant disease comprising rice seedling cotton rot, tomato root rot, potato late blight, tobacco black shank, millet powdery mildew, grape downy mildew, lettuce downy mildew, cucumber downy mildew, or cucumber anthracnose.

12. The method of claim 8, wherein applying an isothiazole oxime ether-containing strobilurin compound to one or more plants or to one or more insects to control a plant disease or a plant pest comprises applying an antiviral composition comprising the isothiazole oxime ether-containing strobilurin compound to the one or more plants to control the plant disease,
the one or more plants comprising rice, wheat, barley, oats, corn, sorghum, sweet potato, potato, cassava, soybean, pea, broad bean, pea, mung bean, adzuki bean, cotton, sericulture, peanuts, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, Rape, onion, garlic, watermelon, melon, cantaloupe, papaya, apple, citrus and peach, tea, wild vegetables, bamboo shoots, hops, pepper, banana, papaya, orchid, or bonsai, and
the plant disease comprising rice dwarf disease, yellow dwarf disease, stripe leaf blight, tomato fern leaf virus disease, pepper mosaic virus disease, tobacco vein necrosis virus disease, corn dwarf mosaic disease, cauliflower mosaic virus, citrus virus disease, orchid leaf Virus, or Jianlan ring spot virus.

13. The method of claim 8, wherein applying an isothiazole oxime ether-containing strobilurin compound to one or more plants or to one or more insects to control a plant disease or a plant pest comprises applying an acaricide composition comprising the isothiazole oxime ether-containing strobilurin compound to the one or more plants to control the plant pest,
the one or more plants comprising rice, wheat, barley, oats, corn, sorghum, sweet potato, potato, tapioca, soybean, pea, broad bean, pea, mung bean, adzuki bean, cotton, sericulture, peanuts, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, beet, Rape, onion, garlic, watermelon, melon, cantaloupe, papaya, apple, citrus and peach, tea, wild vegetables, bamboo shoots, hops, pepper, banana, papaya, orchid, or bonsai, and
the plant pest comprising the genus *Aphididae*, the genus *Diptera*, the *eucalyptus*, the genus *Eucalyptus*, or mites.

14. The method of claim 8, further comprising co-administering the isothiazole oxime ether-containing strobilurin compound with one or more insecticides, one or more fungicides, one or more anti-plant virus agents, or one or more acaricides.

* * * * *